United States Patent
Paul

(10) Patent No.: US 11,004,569 B2
(45) Date of Patent: May 11, 2021

(54) PATIENT SLEEP THERAPY SELF MANAGEMENT TOOL

(71) Applicant: KONINKLIJKE PHILIPS N.V., Eindhoven (NL)

(72) Inventor: Zachary Dean Paul, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 785 days.

(21) Appl. No.: 15/642,786

(22) Filed: Jul. 6, 2017

(65) Prior Publication Data

US 2017/0296762 A1   Oct. 19, 2017

Related U.S. Application Data

(62) Division of application No. 14/405,589, filed as application No. PCT/IB2013/054739 on Jun. 10, 2013, now Pat. No. 9,814,850.

(Continued)

(51) Int. Cl.
*A61M 16/00* (2006.01)
*G16H 80/00* (2018.01)
(Continued)

(52) U.S. Cl.
CPC .......... *G16H 80/00* (2018.01); *A61B 5/4818* (2013.01); *A61M 16/0003* (2014.02);
(Continued)

(58) Field of Classification Search
CPC .......... A61M 16/0003; A61M 5/4818; A61M 16/06; G06F 19/324; G06F 19/3406;
(Continued)

(56) References Cited

U.S. PATENT DOCUMENTS 5,148,802 A   9/1992 Sanders et al.
5,313,937 A   5/1994 Zdrojkowski et al.
(Continued)

FOREIGN PATENT DOCUMENTS

EP   1800705 A2   6/2007

OTHER PUBLICATIONS

"TRENDset Software Manual", Version 1.1.17, XP055080651, Schwerin, Germany, retrieved from the internet: URL:http/://www.ukcpap.co.uk/pdf Trend II Software Manual.PDF, Nov. 1, 2011, pp. 1-88.

(Continued)

*Primary Examiner* — Steven O Douglas

(57) ABSTRACT

A tool is provided for use in conjunction with a pressure support system that is structured to provide therapy to a patient to treat a condition of the patient by delivering a flow of breathing gas to the patient. The tool may be implemented on a portable electronic device or a PC and is configured to, among other things, provide customized/personalized education and feedback to the patient based, at least in part, on data that is measured by the pressure support system during the provision of therapy to the patient. The tool utilizes certain patient/therapy metrics, where each patient/therapy metric includes raw data that was measured by the pressure support system and that has been processed (e.g., summarized and/or otherwise manipulated) to form the patient/therapy metric.

20 Claims, 15 Drawing Sheets

Related U.S. Application Data

(60) Provisional application No. 61/657,204, filed on Jun. 8, 2012.

(51) Int. Cl.
  *G16H 40/63* (2018.01)
  *G16H 15/00* (2018.01)
  *G16H 20/40* (2018.01)
  *G16H 50/70* (2018.01)
  *A61B 5/00* (2006.01)
  *A61M 16/06* (2006.01)

(52) U.S. Cl.
  CPC ............ *A61M 16/06* (2013.01); *G16H 15/00* (2018.01); *G16H 20/40* (2018.01); *G16H 40/63* (2018.01); *G16H 50/70* (2018.01); A61M 2205/52 (2013.01); F04C 2270/041 (2013.01)

(58) Field of Classification Search
  CPC ............ G06F 19/3418; G06F 19/3481; G06F 19/3487; G06F 2205/52; F04C 2270/041
  See application file for complete search history.

(56) References Cited

U.S. PATENT DOCUMENTS

| | | |
|---|---|---|
| 5,433,193 A | 7/1995 | Sanders et al. |
| 5,632,269 A | 5/1997 | Zdrojkowski et al. |
| 5,803,065 A | 9/1998 | Zdrojkowski et al. |
| 6,029,664 A | 2/2000 | Zdrojkowski et al. |
| 6,920,875 B1 | 7/2005 | Hill et al. |
| 8,881,727 B2 * | 11/2014 | Aloia .................... A61M 16/00 128/204.23 |
| 2008/0071580 A1 | 3/2008 | Marcus et al. |
| 2008/0078384 A1 | 4/2008 | Messenger et al. |
| 2012/0024287 A1 | 2/2012 | Aloia et al. |

OTHER PUBLICATIONS

Stepnowsky, "Telemonitoring and sleep apnea: effect of CPAP adherence", VIReC Clinical Informatics Seminar, May 15, 2012, pp. 1-58.

* cited by examiner

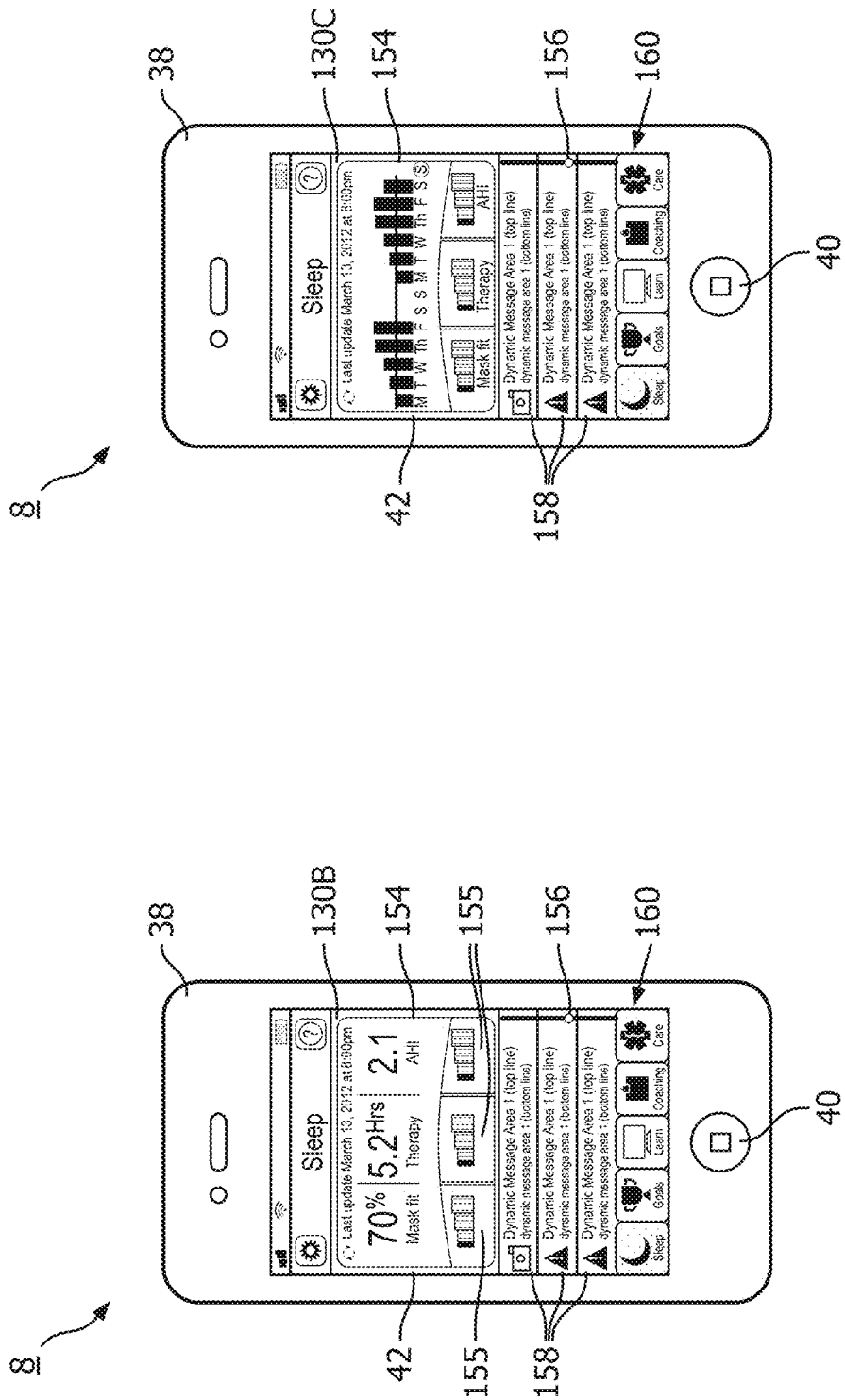

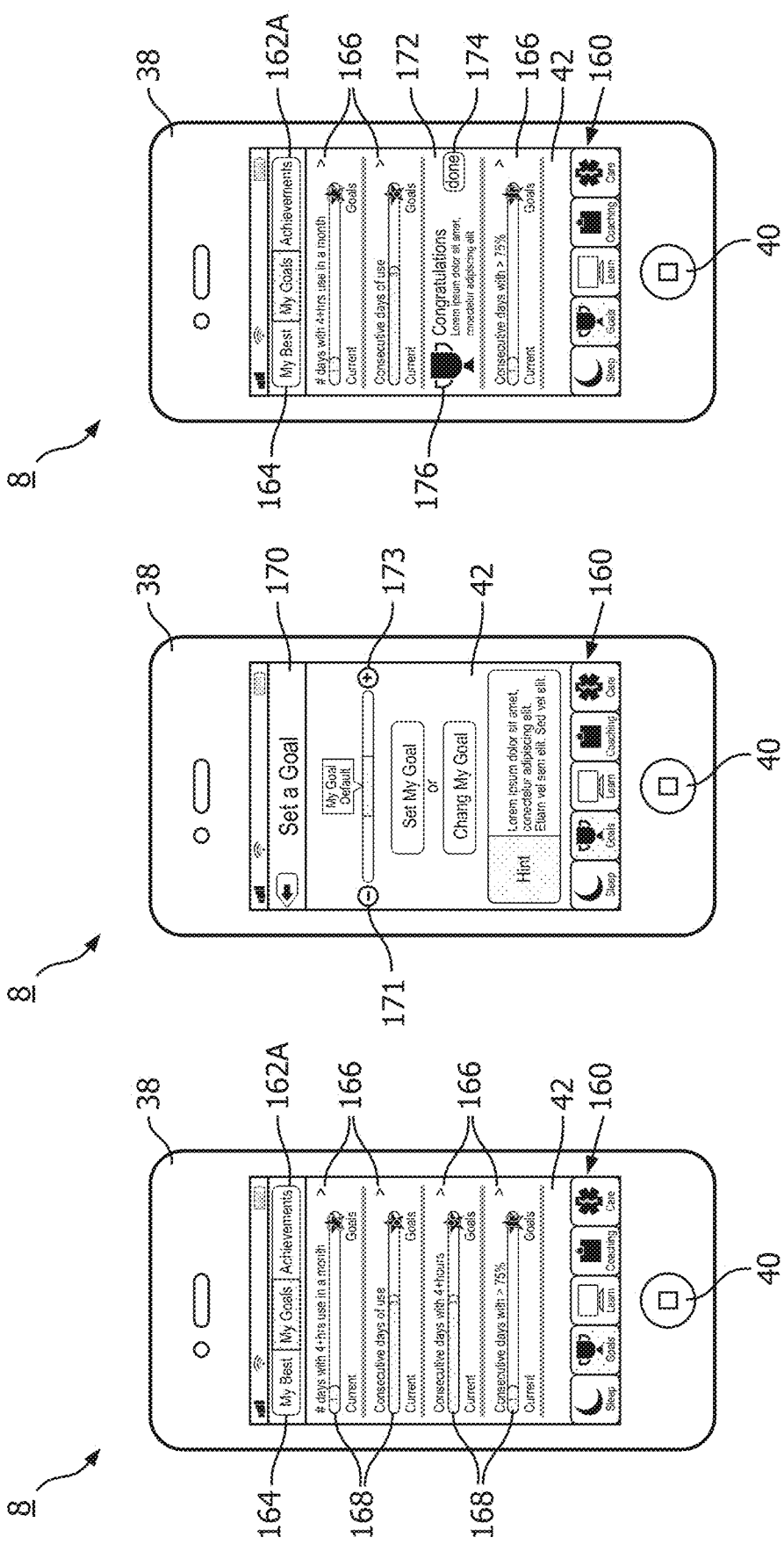

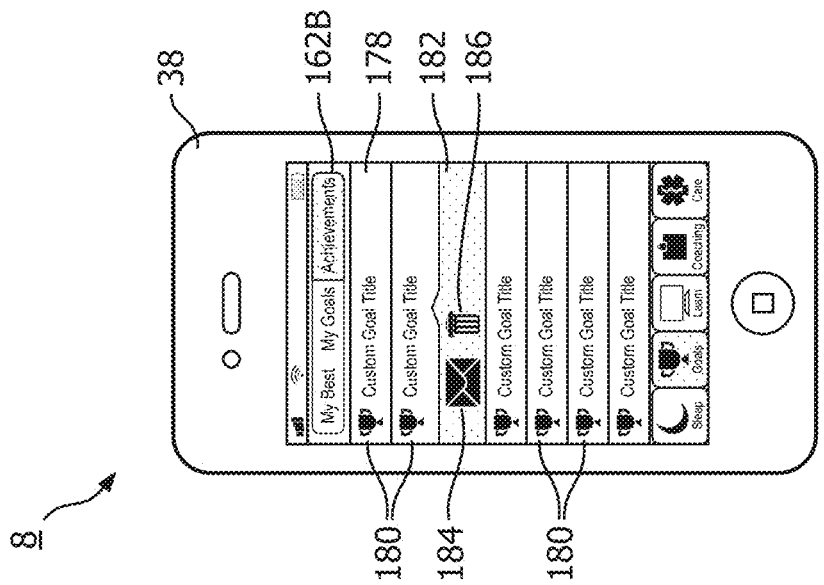
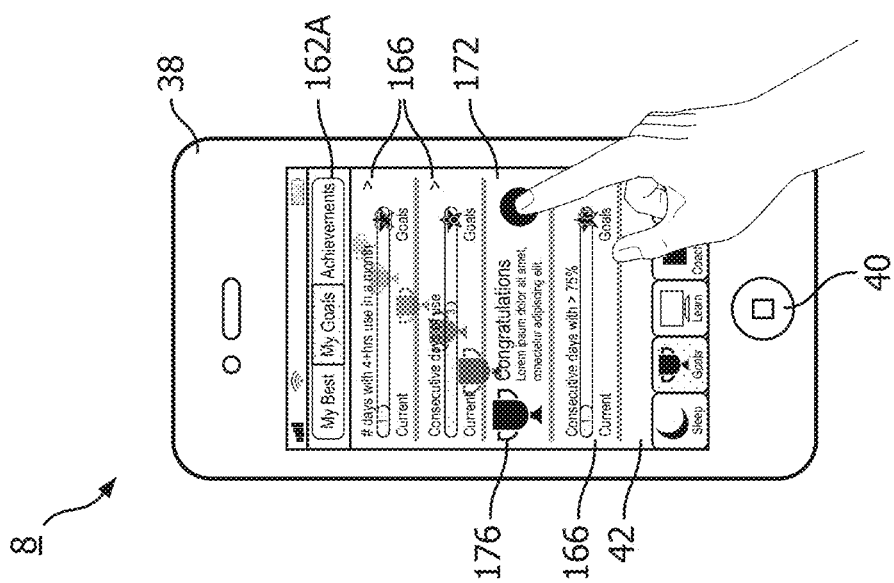
FIG. 19
FIG. 18

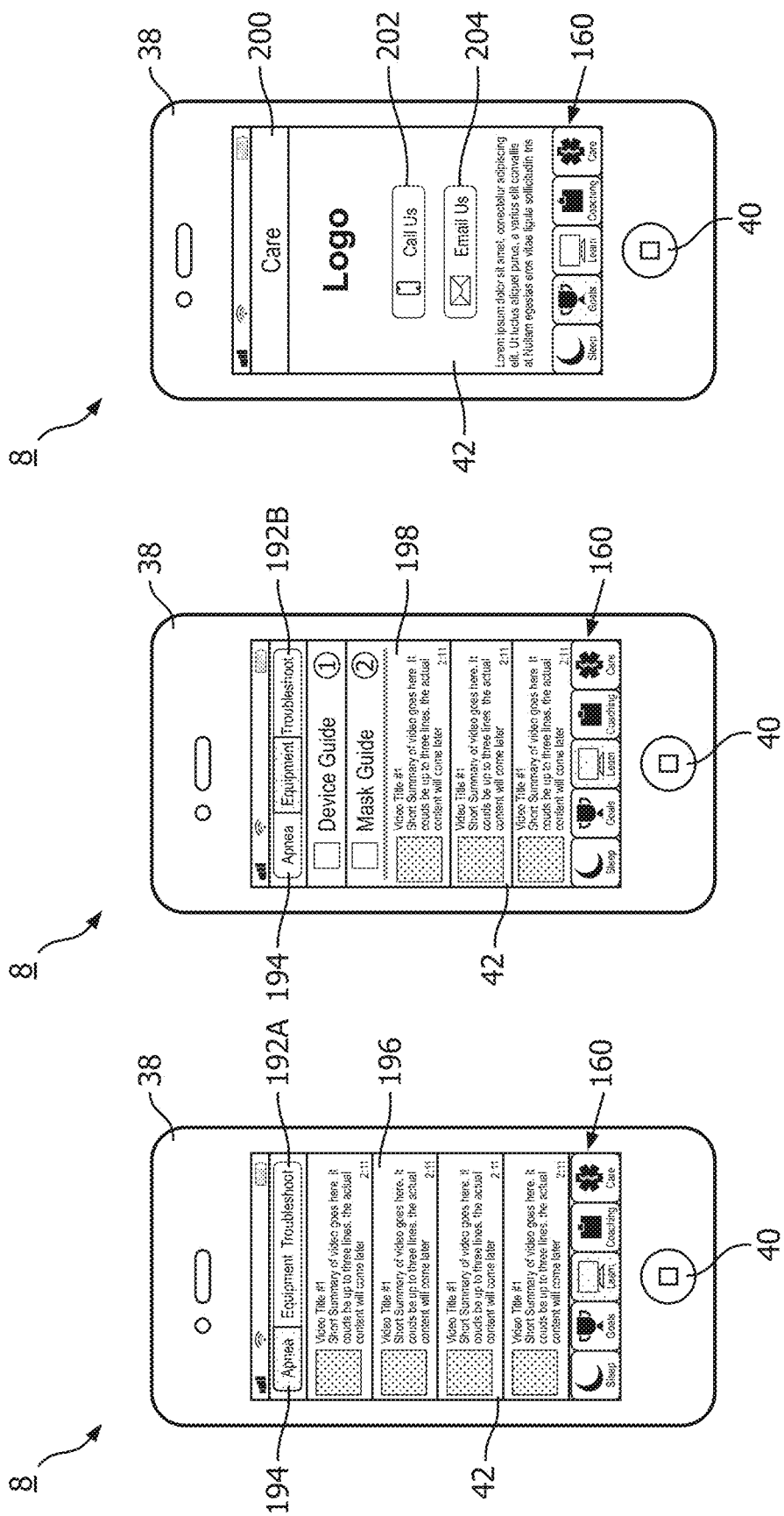

PATIENT SLEEP THERAPY SELF MANAGEMENT TOOL

CROSS-REFERENCE TO PRIOR APPLICATIONS

This application is a divisional application of U.S. National Phase application under 35 U.S.C. § 371, Ser. No. 14/405,589, filed on Dec. 4, 2014, which claims the benefit of International Application Serial No. PCT/IB2013/054739, filed on Jun. 10, 2013, which claims the benefit of U.S. Application Ser. No. 61/657,204, filed on Jun. 8, 2012. These applications are hereby incorporated by reference herein.

BACKGROUND OF THE INVENTION

1. Field of the Invention

The present invention relates to systems for treating conditions, such as sleep disordered breathing, using positive airway pressure (PAP) therapy, and in particular to a tool configured to, among other things, provide customized/personalized education and feedback to the patient relating to their therapy.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of a patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is connected to a gas delivery tube or conduit and interfaces the pressure support device with the airway of the patient, so that a flow of breathing gas can be delivered from the pressure/flow generating device to the airway of the patient.

With the explosive growth of sophisticated portable electronic devices, such as smartphones and tablet PCs, and the increasingly user friendly operating systems that they employ, patients throughout the world are increasingly gaining the ability to easily obtain and share information, such as educational information, and communicate with health care providers. It would thus be advantageous to provide, and there is thus a need for, a system and tool that provides patients the ability to take a more active role in the management of their sleep disordered breathing condition, and therapy being provided using a pressure support system, using their portable electronic device, or, alternatively, a PC.

SUMMARY OF THE INVENTION

In one embodiment, a method of providing information to a patient is provided, wherein the patient uses a pressure support system structured to provide therapy to the patient to treat a condition of the patient by delivering a flow of breathing gas to the patient. The method includes receiving in a computing device first information identifying one or more particular components of the pressure support system, receiving in the computing device second information identifying a data connection methodology by which data measured by the pressure support system during the provision of therapy is to be transferred from the pressure support system to a location where the data is processed, and displaying third information on a display of the computing device, the third information being one of: (i) information relating to use of or care for the pressure support system, (ii) information relating to transferring the data from the pressure support system, and (iii) information relating to one or more solutions for problems relating to use of the pressure support system, the third information being selected based on either one or both of the first information and the second information.

In another embodiment, a computing device configured to provide information to a patient is provided, wherein the patient uses a pressure support system structured to provide therapy to the patient to treat a condition of the patient by delivering a flow of breathing gas to the patient. The computing device includes a display and a processor apparatus including a processor and a memory, the memory storing one or more routines executable by the processor, the one or more routines being adapted to: receive first information identifying one or more particular components of the pressure support system, receive second information identifying a data connection methodology by which data measured by the pressure support system during the provision of therapy is to be transferred from the pressure support system to a location where the data is processed, and display third information on the display, the third information being one of: (i) information relating to use of or care for the pressure support system, (ii) information relating to transferring the data from the pressure support system, and (iii) information relating to one or more solutions for problems relating to use of the pressure support system, the third information being selected based on either one or both of the first information and the second information.

In another embodiment, a method of providing information to a patient is provided, wherein the patient uses a pressure support system structured to provide therapy to the patient to treat a condition of the patient by delivering a flow of breathing gas to the patient. The method includes establishing in a computing device a goal based on a patient/therapy metric relating to treatment using the pressure support system, obtaining in the computing device patient/therapy metric data, wherein the patient/therapy metric data is formed by processing data measured by the pressure support system during the provision of therapy to the patient, and displaying goal information on a display of the computing device, the goal information indicating progress toward the goal and being based on the patient/therapy metric data.

In still another embodiment, a computing device configured to provide information to a patient is provided, wherein the patient uses a pressure support system structured to provide therapy to the patient to treat a condition of the patient by delivering a flow of breathing gas to the patient. The computing device includes a display, and a processor apparatus including a processor and a memory, the memory storing one or more routines executable by the processor, the one or more routines being adapted to: establish a goal based on a patient/therapy metric relating to treatment using the pressure support system, obtain patient/therapy metric data, wherein the patient/therapy metric data is formed by processing data measured by the pressure support system during the provision of therapy to the patient, generate goal information, the goal information indicating progress toward the goal and being based on the patient/therapy metric data, and cause the display to display the goal information.

In yet another embodiment, a method of reporting information relating to use by a patient of a pressure support system structured to provide therapy to the patient to treat a condition of the patient by delivering a flow of breathing gas to the patient is provided. The method includes obtaining patient/therapy metric data in a computing device separate from the pressure support system, wherein the patient/therapy metric data is formed by processing data measured by the pressure support system during the provision of therapy to the patient, and automatically generating in the computing device an electronic message for transmission out of the computing device based on the patient/therapy metric data.

In still another embodiment, a computing device configured to report information relating to use by a patient of a pressure support system structured to provide therapy to the patient to treat a condition of the patient by delivering a flow of breathing gas to the patient is provided. The computing device is separate from the pressure support system and includes a display, and a processor apparatus including a processor and a memory, the memory storing one or more routines executable by the processor, the one or more routines being adapted to: obtain patient/therapy metric data, wherein the patient/therapy metric data is formed by processing data measured by the pressure support system during the provision of therapy to the patient, and automatically generate an electronic message for transmission out of the computing device based on the patient/therapy metric data.

In another embodiment, a method of establishing an account for a user of a system for providing information to a patient is provided, wherein the patient uses a pressure support system structured to provide therapy to the patient to treat a condition of the patient by delivering a flow of breathing gas to the patient. The method includes receiving in a computing device username information for the user and device identifying information for identifying a component of the pressure generating system, transmitting the username information and the device identifying information to a location remote from the computing device and the pressure generating system, determining at the remote location whether the username information is unique to the system and whether the device identifying information is valid, and establishing the account only if it is determined that both the username information is unique to the system and the device identifying information is valid.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIGS. 5-24 are schematic diagrams showing a number of "screen shots" of a touchscreen display of the portable electronic device of FIGS. 1, 3 and 4 that demonstrate the operation and functionality of the software application/tool of the present invention.

DETAILED DESCRIPTION OF EXEMPLARY EMBODIMENTS

Figure 1:
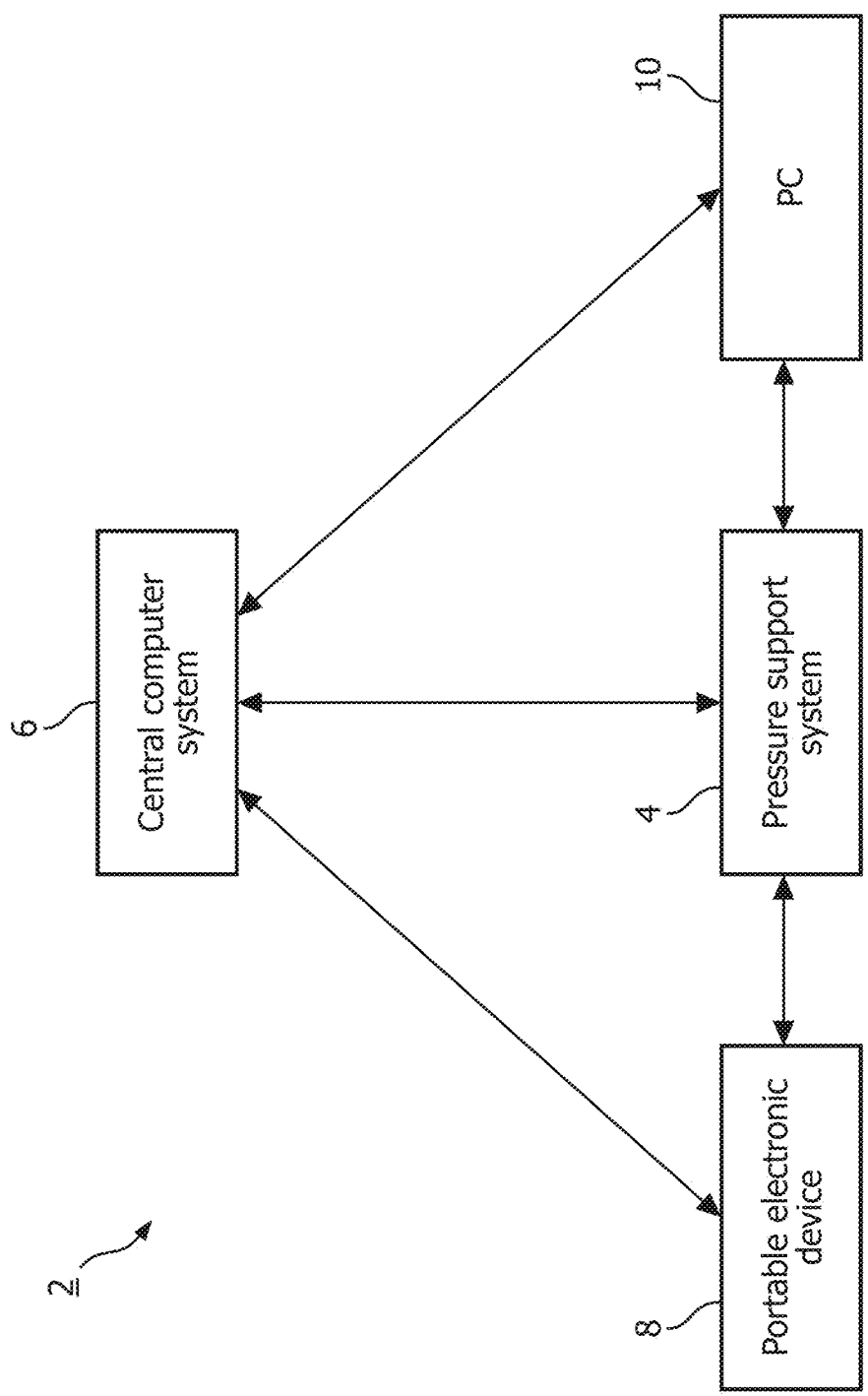
FIG. 1 is a block diagram of a system for treating sleep disordered breathing and monitoring and managing the treatment according to one non-limiting exemplary embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a block diagram of a system 2 for treating sleep disordered breathing and monitoring and managing the treatment according to one non-limiting exemplary embodiment of the present invention. As seen in FIG. 1, system 2 includes a number of individual components that, as described in greater detail herein, together provide a mechanism for a patient suffering from a sleep disordered breathing condition, such as OSA, to effectively manage their disease and treatment by providing customized/personalized education and feedback regarding their disease and their specific therapy and by increasing therapy compliance. In particular, system 2 includes a pressure support system 4, a central computer system 6, a portable electronic device 8, and a personal computer (PC) 10, each of which is described in greater detail below, which together provide a sleep disordered breathing treatment and self management mechanism.

Pressure support system 4 shown in FIG. 1 is a system structured to provide positive airway pressure (PAP) support therapy to a patient in order to treat that patient's sleep disordered breathing condition. One suitable non-limiting example of pressure support system 4 that may be used in system 2 is described in detail herein in connection with FIG. 2. Central computer system 6 in the exemplary embodiment shown in FIG. 1 comprises a system of one or more server computers and one or more databases that are structured and configured to store and process patient data collected by and received from pressure support system 4 (and from similar pressure support systems of other patients) so that the data may be accessed by one or more of the patient, the patient's homecare provider and/or the patient's physician. Portable electronic device 8 shown in FIG. 1 is a device such as, without limitation, a smartphone, a tablet PC, or some other portable computing device. One suitable example of portable electronic device 8 that may be used in system 2 is described in detail herein in connection with FIGS. 3 and 4.

Figure 3:
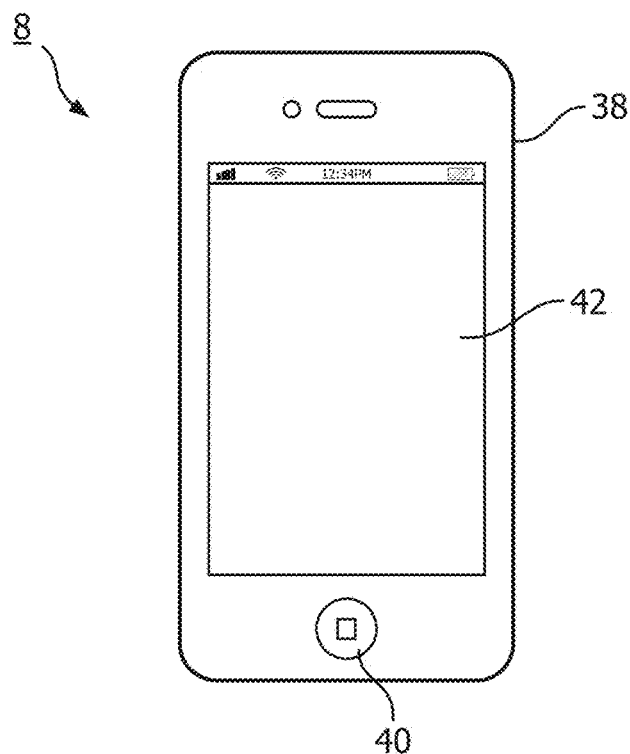
FIGS. 3 and 4 are schematic diagrams of an exemplary portable electronic device that may be used in implementing the system of FIG. 1.
Figure 4:
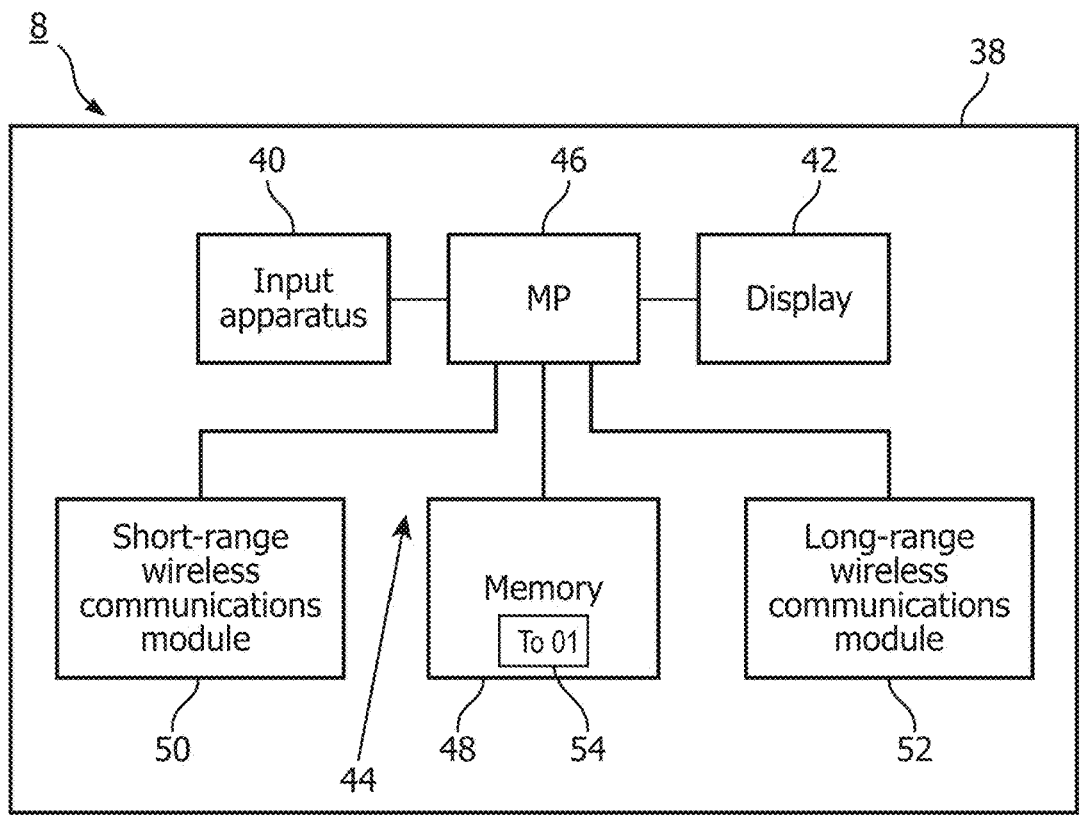

In addition, as described in detail herein, the present invention provides a tool in the form of a software application that may be implemented on either or both of portable electronic device 8 and PC 10 that is configured to, among other things, provide the customized/personalized education and feedback noted above to the patient based, at least in part, on data that is measured by pressure support system 4 during the provision of therapy to the patient. For ease of illustration, the tool of the present invention will be described as implemented on an exemplary portable electronic device 8 (FIGS. 3 and 4). It will be understood, however, that that particular implementation is meant to be exemplary only, and that the concepts of the present invention, and in particular the software application described herein, may be implemented on a portable electronic device 8 in other suitable forms and/or in a suitable form on PC 10.

Figure 2:
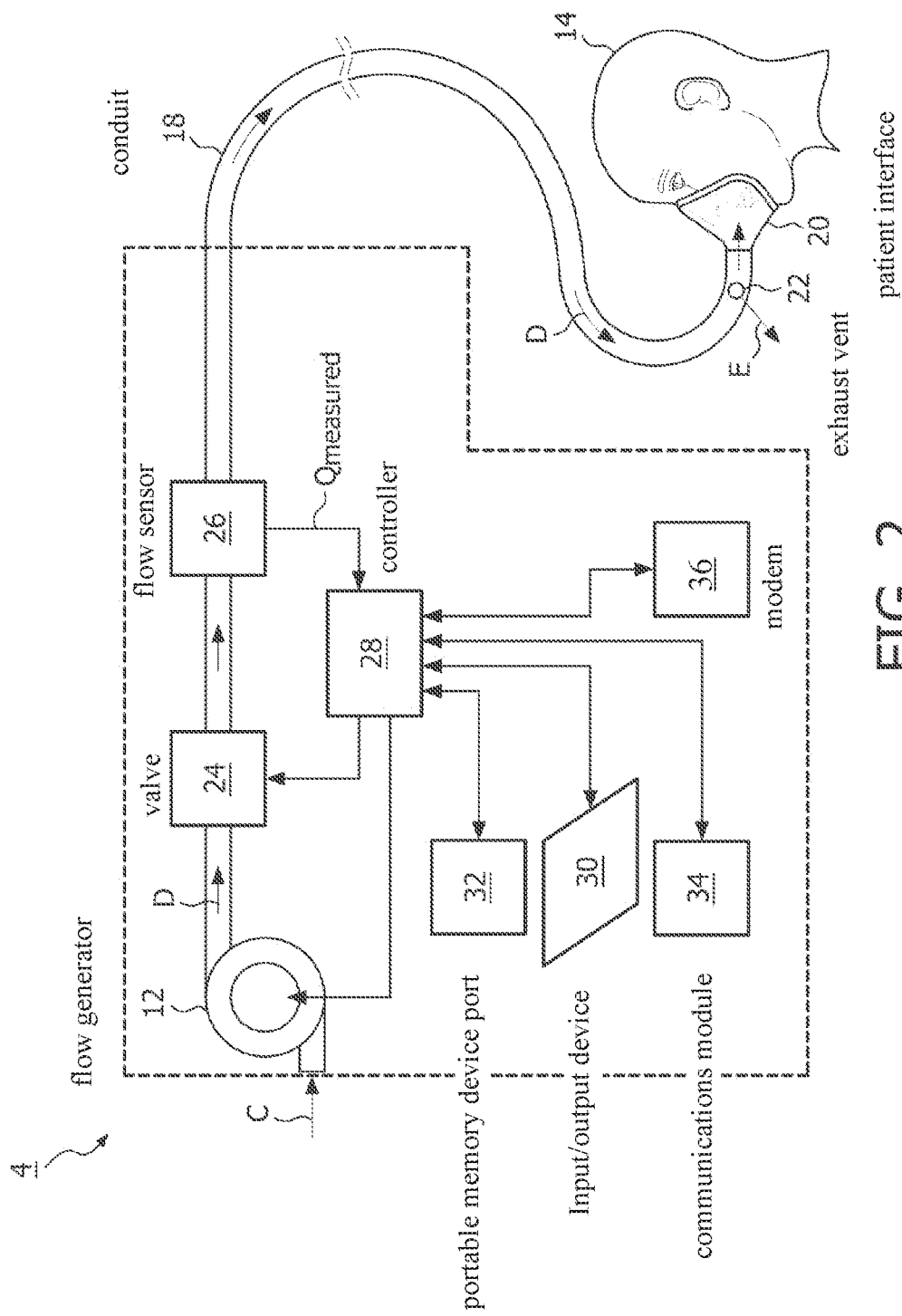
FIG. 2 is a schematic diagram of a pressure support system according to one particular, non-limiting exemplary embodiment that may be used in implementing the system of FIG. 1.

FIG. 2 is a schematic diagram of pressure support system 4 according to one particular, non-limiting exemplary embodiment that may be used in implementing system 2. Referring to FIG. 2, pressure support system 4 includes a gas flow generator 12, such as a blower used in a conventional CPAP or bi-level pressure support device, which receives breathing gas, generally indicated by arrow C, from any suitable source, e.g., a pressurized tank of oxygen or air, the ambient atmosphere, or a combination thereof. Gas flow generator 12 generates a flow of breathing gas, such as air, oxygen, or a mixture thereof, for delivery to an airway of patient 14 at relatively higher and lower pressures, i.e., generally equal to or above ambient atmospheric pressure. The pressurized flow of breathing gas, generally indicated by arrow D from gas flow generator 12, is delivered via a delivery conduit 18 to a breathing mask or patient interface 20 of any known construction, which is typically worn by or otherwise attached to patient 14 to communicate the flow of breathing gas to the airway of patient 14. Delivery conduit 18 and patient interface device 20 are typically collectively referred to as a patient circuit.

Pressure support system 4 shown in FIG. 2 is what is known as a single-limb system, meaning that the patient circuit includes only delivery conduit 18 connecting patient 14 to pressure support system 4. As such, exhaust vent 22 is provided in delivery conduit 18 for venting exhaled gasses from the system as indicated by arrow E. It should be noted that exhaust vent 22 can be provided at other locations in addition to or instead of in delivery conduit 18, such as in patient interface device 20. It should also be understood that exhaust vent 22 can have a wide variety of configurations depending on the desired manner in which gas is to be vented from pressure support system 4.

The present invention also contemplates that pressure support system 4 can be a two-limb system, having a delivery conduit and an exhaust conduit connected to patient 14. In a two-limb system (also referred to as a dual-limb system), the exhaust conduit carries exhaust gas from patient 14 and includes an exhaust valve at the end distal from patient 14. The exhaust valve in such an embodiment is typically actively controlled to maintain a desired level or pressure in the system, which is commonly known as positive end expiratory pressure (PEEP).

Furthermore, in the illustrated exemplary embodiment shown in FIG. 2, patient interface 20 is a nasal/oral mask. It is to be understood, however, that patient interface 20 can include a nasal mask, a pillows style nasal cushion, a cradle style nasal cushion, a full face mask, any other device that provides a suitable gas flow communicating function. Also, for purposes of the present invention, the phrase "patient interface" can include delivery conduit 18 and any other structures that connect the source of pressurized breathing gas to patient 14.

In the illustrated embodiment, pressure support system 4 includes a pressure controller in the form of a valve 24 provided in delivery conduit 18. Valve 24 controls the pressure of the flow of breathing gas from flow generator 12 delivered to patient 14. For present purposes, flow generator 12 and valve 24 are collectively referred to as a pressure generating system because they act in concert to control the pressure and/or flow of gas delivered to patient 14. However, it should be apparent that other techniques for controlling the pressure of the gas delivered to patient 14, such as varying the blower speed of flow generator 12, either alone or in combination with a pressure control valve, are contemplated by the present invention. Thus, valve 24 is optional depending on the technique used to control the pressure of the flow of breathing gas delivered to patient 14. If valve 24 is eliminated, the pressure generating system corresponds to flow generator 12 alone, and the pressure of gas in the patient circuit is controlled, for example, by controlling the motor speed of flow generator 12.

Pressure support system 4 further includes flow sensor 26 that measures the flow of the breathing gas within delivery conduit 18. In the particular embodiment shown in FIG. 2, flow sensor 26 is interposed in line with delivery conduit 18, most preferably downstream of valve 24. Flow sensor 26 generates a flow signal $Q_{MEASURED}$ that is provided to controller 28 and is used by controller 28 to determine the flow of gas at patient 14, referred to as $Q_{PATIENT}$. Of course, other techniques for measuring the respiratory flow of patient 14 are contemplated by the present invention, such as, without limitation, measuring the flow directly at patient 14 or at other locations along delivery conduit 18, measuring patient flow based on the operation of flow generator 12, and measuring patient flow using a flow sensor upstream of valve 24. In addition, it should be noted that flow sensor 26 may be omitted (i.e., it is optional), and that other techniques may be used to estimate flow. For example, flow may be estimate using motor parameters (e.g. motor current). Furthermore, many aspects of the invention as described herein do not require flow monitoring per se and could be done with simple measurements like blower power consumption or blower hours. Also, most modern pressure support system implementations include pressure sensors, which may be used to control the pressure at the outlet of the device (and, by extension, the pressure at the patient) as well as to perform other monitoring tasks (e.g. monitor acoustic signal for snoring).

Controller 28 may be, for example, a microprocessor, a microcontroller or some other suitable processing device, that includes or is operatively coupled to a memory (not shown) that provides a storage medium for data and software executable by controller 28 for controlling the operation of pressure support system 4. Input/output device 30 is provided for setting various parameters used by pressure support system 4, as well as for displaying and outputting information and data to a user, such as a clinician or caregiver.

In the exemplary embodiment, which is a single-limb system, controller 28 estimates the leakage of gas from pressure support system 4 using any suitable technique and incorporates this leak estimation into the determination of the actual patient flow. This leak estimation is required in a single-limb system, because a single-limb system includes a known leak through the exhaust vent as well as other unknown leaks, such as leaks at the patient contact site of the patient interface and at various conduit couplings on the patient circuit. In a two-limb system, leak estimation may not be required, because a flow sensor is typically provided at the exhaust vent to measure, directly, the flow of exhaust gas. In such a system, the patient flow can be determined by subtracting the measured exhaust flow from the measured flow delivered to the patient. It can be appreciated that leak detection can be performed in a two-limb system to increase the accuracy of the patient flow determination. U.S. Pat. No. 5,148,802 to Sanders et al., U.S. Pat. No. 5,313,937 to Zdrojkowski et al., U.S. Pat. No. 5,433,193 to Sanders et al., U.S. Pat. No. 5,632,269 to Zdrojkowski et al., U.S. Pat. No. 5,803,065 to Zdrojkowski et al., U.S. Pat. No. 6,029,664 to Zdrojkowski et al., and U.S. Pat. No. 6,920,875 to Hill et al., the contents of each of which are incorporated herein by reference, describe how to accomplish the necessary functions in order to provide separate IPAP and EPAP levels to the patient. These functions include techniques for detecting and estimating leak, and techniques for detecting the respiratory state of a patient (FE), and managing, e.g., triggering and cycling, the bi-level delivery of breathing gas to the patient in the presence of leaks. Thus, a detailed discussion of these functions is omitted from the present application for the sake of simplicity and brevity.

Finally, pressure support system 4 in the exemplary embodiment includes a portable memory device port 32, a short range wireless communications module 34, and a modem 36, all of which are operatively coupled to controller 28. Portable memory device port 32 is structured to enable a portable memory device to be selectively coupled to pressure support system 4 so that data can be written to and read from the portable memory device. In the exemplary embodiment, portable memory device port 32 is an SD card port and the portable memory device is an SD card, although other devices/technologies, such as, without limitation, a USB port and a USB-type portable memory device, may also be used. Short range wireless communications module 34 is a module that is structured and configured to enable pressure support system 4 to communicate with other, similarly equipped electronic devices (e.g., portable electronic device 8 as described herein) over a short range wireless network. In the exemplary embodiment, short range wireless communications module 34 is a Bluetooth® module that is structured and configured to enable pressure support system 4 to communicate with other devices over an ad hoc Bluetooth® network. In addition, short range wireless communications module 34 may be incorporated within pressure support system 4, or may be a module that is selectively connectable to pressure support system 4 via a USB port or other suitable connection. Modem 36 is structured and configured to enable pressure support system 4 to communicate with central computer system 6 over a suitable network, such as the Internet. Modem 36 may employ a wired connection, a wireless connection, or some combination thereof. It should be noted that, while a number of different communication methods have been described, in the present invention, only at least one method of communicating with portable electronic device 8 or PC 10 is necessary.

An exemplary portable electronic device 8 that may be used in system 2 is indicated generally in FIG. 3 and is depicted schematically in FIG. 4. The exemplary portable electronic device 8 is a smartphone and includes a housing 38, an input apparatus 40 (which in the illustrated embodiment is a button), a touchscreen display 42, and a processor apparatus 44 disposed in housing 38. A user is able to provide input into processor apparatus 44 using input apparatus 40 and touchscreen display 42. Processor apparatus 44 provides output signals to touchscreen display 42 to enable touchscreen display 42 to display information to the user as described in detail herein.

Processor apparatus 44 comprises a processor 46 and a memory 48. Processor 46 may be, for example and without limitation, a microprocessor (µP) that interfaces with memory 48. Memory 48 can be any one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. Memory 48 has stored therein a number of routines that are executable by processor 46. One or more of the routines implement (by way of computer/processor executable instructions) the software application/tool discussed briefly above and described in greater detail below that is configured to, among other things, provide the customized/personalized education and feedback to the patient based, at least in part, on data that is measured by pressure support system 4 during the provision of therapy to the patient. In the exemplary embodiment, that software application/tool, labeled 54 in FIG. 4 for ease of reference, may be downloaded to portable electronic device 8 from any suitable source, such as an online "app store."

As seen in FIG. 4, portable electronic device 8 also includes a short range wireless communications module 50 that is structured and configured to enable portable electronic device 8 to communicate with other, similarly equipped electronic devices, including pressure support system 4, over a short range wireless network. As noted elsewhere herein, in the exemplary embodiment, short range wireless communications module 50 is a Bluetooth® module that that is structured and configured to enable portable electronic device 8 to communicate with pressure support system 4 over an ad hoc Bluetooth® network. Portable electronic device 8 also includes a long range wireless communications module 52 (e.g., a modem) that is structured and configured to enable portable electronic device 8 to communicate with central computer system 6 over a suitable network, such as the Internet. In the exemplary embodiment, portable electronic device 8 communicates wirelessly with central computer system 6, although a wired connection is also possible. In addition, portable electronic device 8 may also include one or more additional modules/components that provide additional functionality. For example, and without limitation, portable electronic device 8 may include a digital camera (e.g., for barcode reading and/or image capturing for component identification as described herein) and/or other I/O components, such as, without limitation, a microphone, a speaker and/or other audio I/O components for used in playing videos as described herein.

As noted above, portable electronic device 8 implements a software application/tool 54 that is configured to, among other things, provide customized/personalized education and feedback to the patient based, at least in part, on data that is measured by pressure support system 4 during the provision of therapy to the patient. As described in greater detail herein, that software application/tool 54 utilizes certain patient/therapy metrics, wherein each patient/therapy metric comprises raw data that was measured by pressure support system 4 and that has been processed (e.g., summarized and/or otherwise manipulated) to form the patient/therapy metric. In the non-limiting exemplary embodiment described herein to illustrate the present invention, the processing of the raw data into the patient/therapy metrics occurs at central computer system 6, with the patient/therapy metric data then being provided to portable electronic device 8 for use by software application/tool 54 (the patient/therapy metric data is transmitted over a long range network to long range wireless communications module 52 of portable electronic device 8). It will be understood, however, that such a configuration is exemplary only, and that, in alternative embodiments, the processing of the raw data into the patient/therapy metrics may occur in other components/locations, such as, without limitation, in pressure support system 4, in PC 10, in portable electronic device 8, or in some combination thereof.

Referring again to the non-limiting exemplary embodiment described above wherein the processing of the raw data into the patient/therapy metrics occurs at central computer system 6, there thus must be a way for the raw data to periodically (e.g., daily) be provided to central computer system 6. In the exemplary embodiment of system 2, this may be done in any of the following three ways. First, the raw data may be transmitted directly from pressure support system 4 to central computer system 6 using modem 36. Alternatively, the raw data may be transmitted from pressure support system 4 to portable electronic device 8 over a short range wireless network (Bluetooth® in the exemplary embodiment) using short range wireless communications module 34 of pressure support system 4 and short range wireless communications module 50 of portable electronic device 8. The raw data may then be transmitted from portable electronic device 8 to central computer system 6 over a long range network using long range wireless communications module 52 of portable electronic device 8. As another alternative, the raw data may be transferred from pressure support system 4 to PC 10 using a portable memory device (an SD card in the exemplary embodiment). The raw data may then be transmitted from PC 10 to central computer system 6 over a suitable network, such as the Internet. As described in detail herein, the user of software application/tool 54 is able to specify which of these data transfer methodologies they prefer to use.

The operation and functionality of software application/tool 54 according to one exemplary embodiment will now be described in detail. In the following description, that operation and functionality will be described in conjunction with a number of "screen shots" of touchscreen display 42 of portable electronic device 8 which each comprise a state of touchscreen display 42 as determined by software application/tool 54. As noted elsewhere herein, the operation and functionality of software application/tool 54 may also be implemented, in a suitable form, on PC 10, and thus the display of PC 10, in such an implementation, may be caused to display the same or similar "screen shots".

Figures 5, 6:
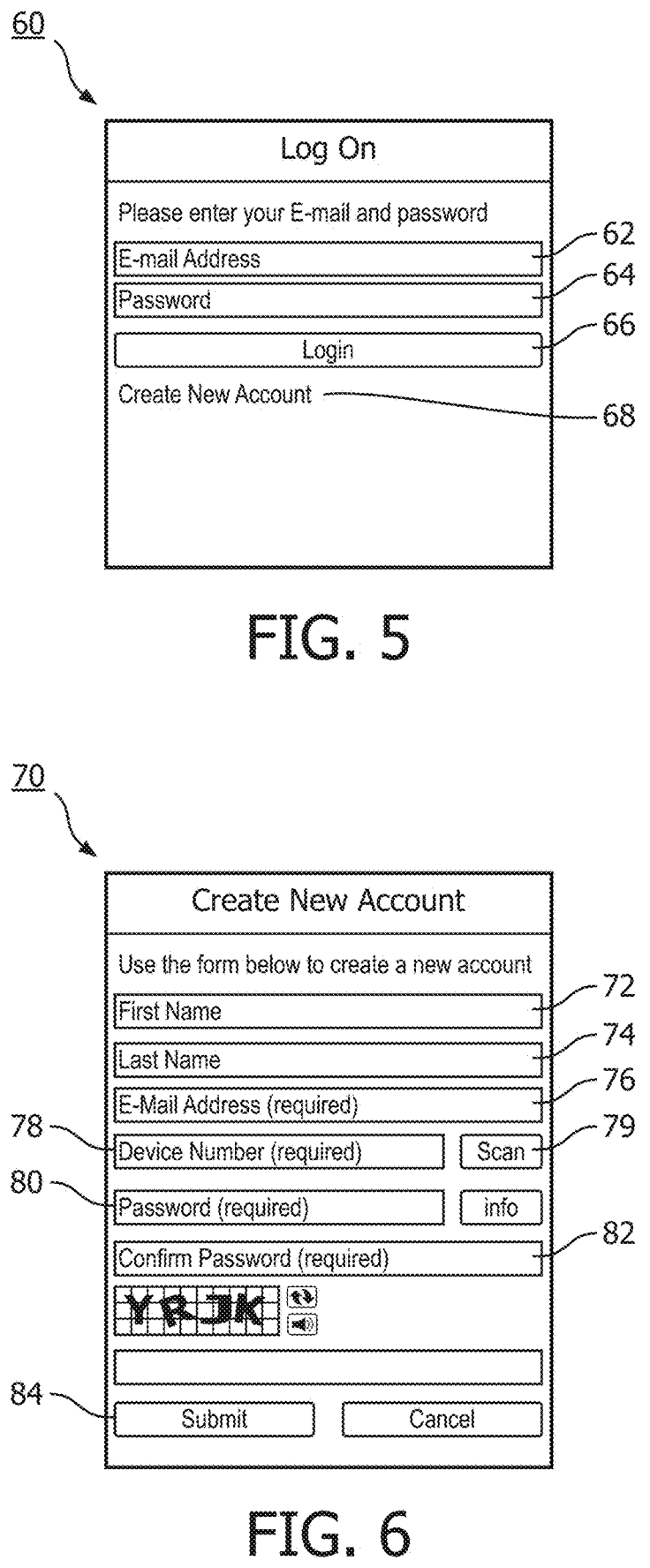

FIG. 5 is a schematic representation of a login screen 60 of software application/tool 54 that is displayed whenever a user launches software application/tool 54. If a user has already established an account, the user can login to software application/tool 54 by entering his or her established account information, including email address and password, in boxes 62 and 64 and selecting login button 66. If, however, the user is a new user of software application/tool 54 without an established account, the user may select the "Create New Account" link 68. In response to selection of the "Create New Account" link 68, software application/tool 54 will cause a create new account screen 70 shown in FIG. 6 to be displayed. In order to create a new account, the user must enter certain information into create new account screen 70. In particular, the user must enter his or her name into boxes 72 and 74 and his or her email address into box 76. In the exemplary embodiment, the email address that is entered must be unique to system 2 and is used as the user's "username." The user is also required to enter a "Device Number" into box 78. The "Device Number" is the serial number of the pressure generating component of pressure support system 4 being used by the user in system 2. The "Device Number" may be entered manually by the user (i.e., typed in using touchscreen display 42) or may be scanned using a barcode provided on pressure support system 4 and a suitable barcode scanning/reading application loaded onto portable electronic device 8 or provided as part of software application/tool 54. In the illustrated, exemplary embodiment, such a barcode scanning/reading application is triggered by selecting scan button 79 shown in FIG. 6. Other methods of obtaining/entering the "Device Number" are also contemplated, such as, without limitation, capturing an image of the serial number portable electronic device 8 and using optical character recognition (e.g., in an application loaded onto portable electronic device 8 or provided as part of software application/tool 54) to extract the "Device Number" or a Bluetooth® or Wi-Fi scan of the local area to load the "Device Number." In the exemplary embodiment, the entered "Device Number" does not need to be unique in system 2. Rather, it may be for a device that has been "recycled," meaning that it was previously used with a first, prior email address (username) and is now being used with another, current email address (username). System 2 does, however, in the exemplary embodiment require that the entered "Device Number" be recognized by system 2 as being valid, meaning that it falls within a predetermined range of a known model pressure support system 4. The user is also required to enter and confirm a password to be used with his or her account in boxes 80 and 82 shown in FIG. 6. Thus, when a user attempts to create an account by entering the information (including an email address and "Device Number") as just described (and selecting submit button 84), central computer system 6 will check whether the email address is unique and whether the "Device Number" is valid, and will authorize the creation of the account only if it is determined that the email address is unique and that the "Device Number" is valid. If either of these checks fail, the user may be informed of the issue and may be redirected to a help portion of software application/tool 54 or to a help website.

Figure 7:
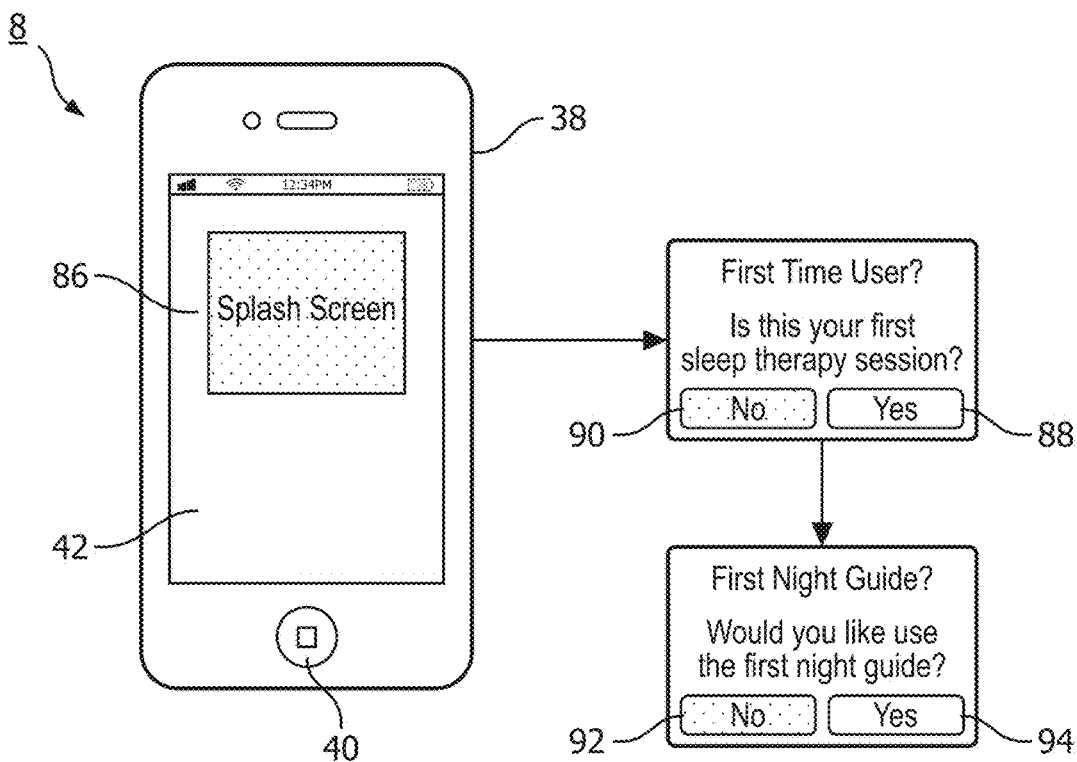

During the first use of software application/tool 54 by the user, after creating a new account as just described, a first use screen 86 will be displayed on touchscreen display 42 as seen in FIG. 7. As shown in FIG. 7, the user will be asked whether this is the first time they have used pressure support system 4 (i.e., whether this is their first therapy session). If they indicate "Yes" by selecting button 88, software application/tool 54 will proceed to the "First Night Guide" portion thereof that is described in detail below. If they indicate "No" by selecting button 90, they will be given the opportunity to still proceed to the "First Night Guide" portion by selecting either button 92 or 94.

Figure 8:
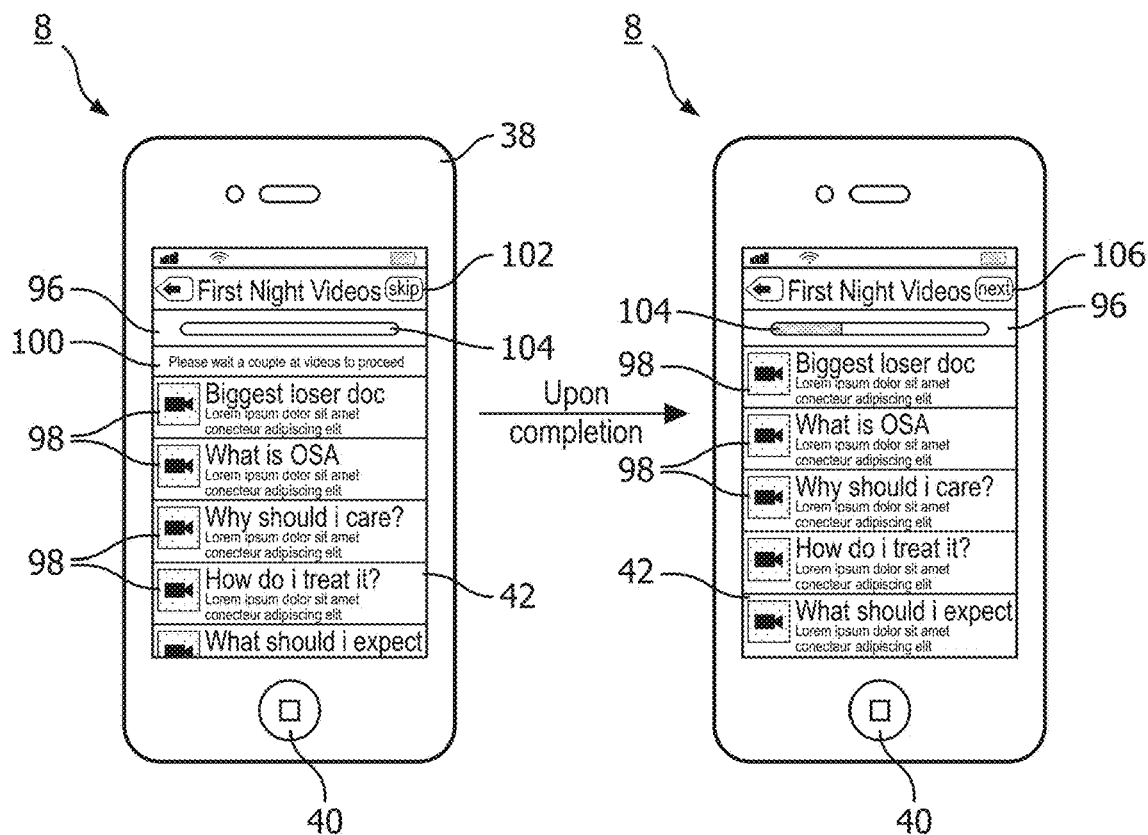

The "First Night Guide" portion of software application/tool 54 is designed to provide education to the user regarding his or her particular sleep disordered breathing condition (e.g., OSA) and regarding the particulars of the pressure support system 4 he or she is going to be using to provide PAP therapy. In a first section of the "First Night Guide" portion, a first night videos screen 96 is provided on touchscreen display 42 as seen in FIG. 8. First night videos screen 96 provides links to a number of videos relating to the user's sleep disordered breathing condition and treatment therefor that may be accessed by the user by selecting an associated icon 98. In the exemplary embodiment, each of the icons 98 is a link to a site (e.g., a third party content sharing sited such as, without limitation, YouTube® or a site maintained by the provider of software application/tool 54 or pressure generating system 4 or by a healthcare provider or a durable medical equipment (DME) supplier) where the video may be accessed. As will be appreciated, the actual video that is accessed via the link may be updated/changed dynamically (i.e., the content may be dynamically updated). Also in the exemplary embodiment, software application/tool 54 recommends, via banner 100, that the user play at least one video in order to advance to the next section of the "First Night Guide" portion. Selecting a skip button 102 enables the user to skip this first section. A progress bar 104 is displayed on first night videos screen 96 indicating to the user the number of steps that remain in the "First Night Guide" portion. In addition, as seen in FIG. 8, once a video is viewed, a "check" icon indicates its completion. Also, once a video is viewed, a next button 106 is provided to enable the user to advance to the next section of the "First Night Guide" portion.

Figure 9:
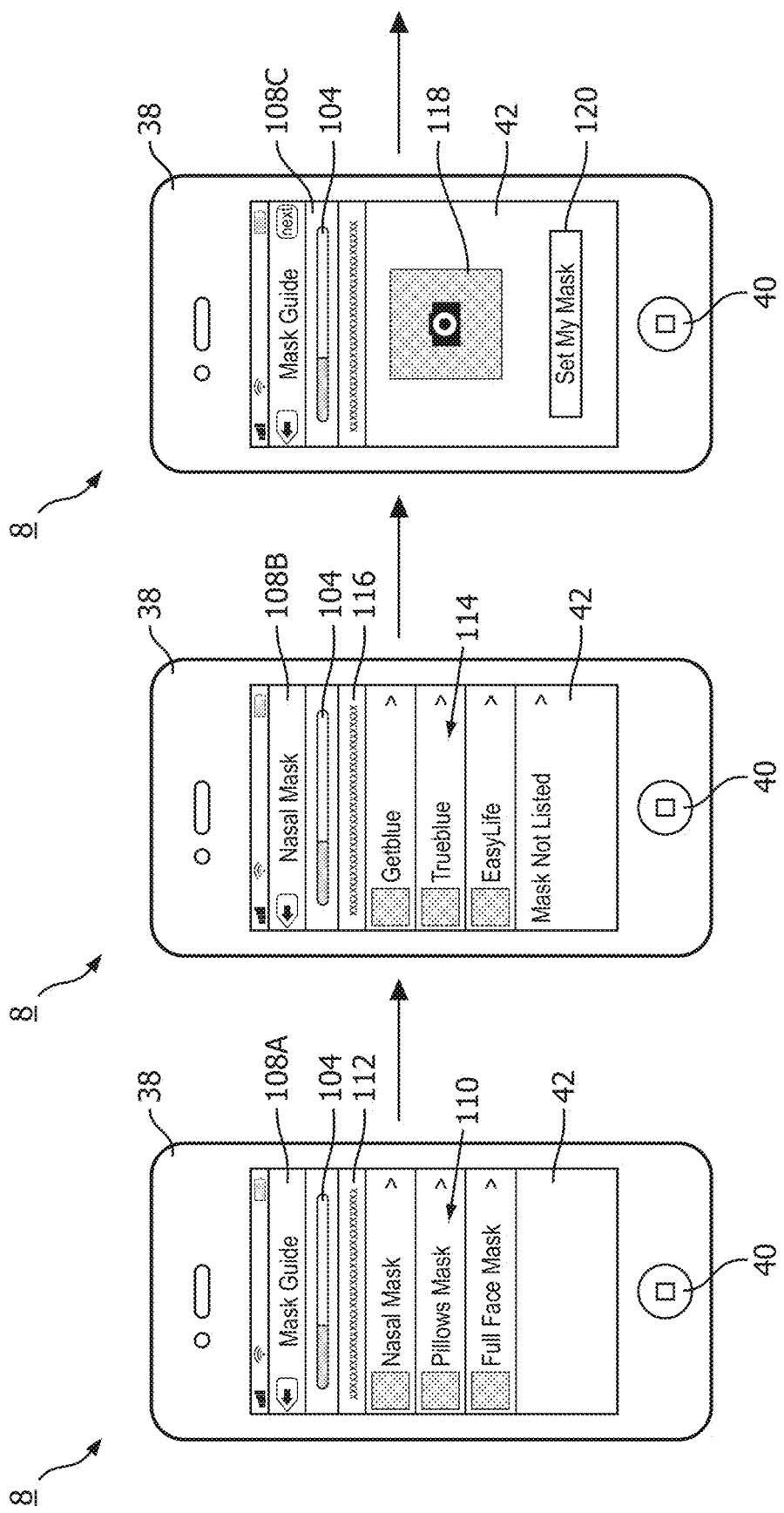
Figure 9:
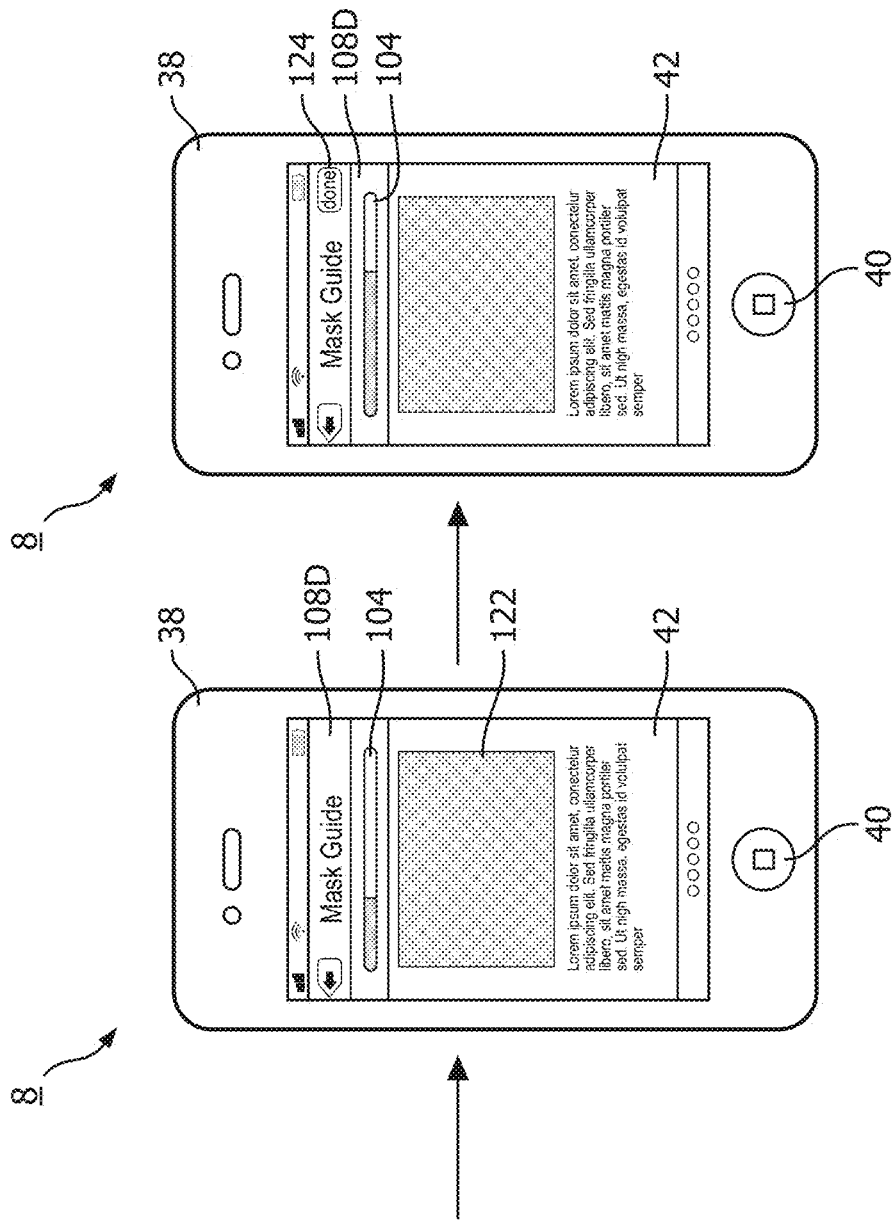

In a second section of the "First Night Guide" portion, called the "Mask Guide" section, the user indicates to software application/tool 54 the type of breathing mask or patient interface 20 (FIG. 2) that he or she is using in pressure support system 4, and based on that information, software application/tool 54 provides information to the user regarding the particular breathing mask or patient interface 20. This process is illustrated in FIG. 9, which shows the progression through a number of exemplary mask guide screens 108 provided on touchscreen display 42. As seen in FIG. 9, a first mask guide screen 108A provides a listing 110 of different mask types (e.g. nasal, pillows, full face) for the user to select from. A banner 112 instructs the user to select their mask type from the listing 110. Once a mask type from listing 110 is selected, a second mask guide screen 108B provides a listing 114 of particular mask models (e.g., by brand name or manufacturer/model no.) for the user to choose from. A banner 116 instructs the user to select their mask model from the listing 114. Once a mask model from listing 114 is selected, a third mask guide screen 108C provides an image 118 of the selected mask model. A button 120 is provided on third mask guide screen 108C to enable the user to set the mask model if correct. Responsive to selecting button 120 (i.e., setting the particular mask model), a fourth mask guide screen 108D is provided that includes a mask guide 122 that is selected based on and corresponds to the set mask model (i.e., once the mask model is set, a call is made in software application/tool 54 accessing the appropriate mask guide 122). Mask guide 122 provides information relating to the set mask model and the use thereof, and may include, without limitation, text, photos, drawings, step by step instructions and/or videos. Fourth mask guide screen 108D also includes a done button 124 that, when selected, enables the user to advance to the next section of the "First Night Guide" portion.

In the illustrated embodiment described above, the mask type and model is specified using manual user input. In alternative embodiments, mask type and model may be discovered/recognized automatically using a number of different technologies, such as, without limitation, reading a bar code provided on mask or patient interface 20 using portable electronic device 8, or capturing a digital image of the mask or patient interface 20 using portable electronic device 8 (i.e., with a digital camera provided therein) and using recognition software provided on portable electronic device 8 to identify the mask type and model from the captured image. In addition, other components of pressure support system 4 (e.g., the gas delivery hose, a humidifier, one or more filters, etc.) may also be identified to software application/tool 54 by manual entry and/or automatic discovery/recognition as just described. Other particular methods of component identification are also possible, such as, without limitation, using photos (images) of packaging material, photos (images) of a gas delivery hose, QR barcodes, text recognition on a hose/mask, searching for Bluetooth® or other wireless-enabled masks, and identification of components (e.g., mask) through querying the pressure generating device (e.g. CPAP) if it has already knowledge of the component.

Figure 10:
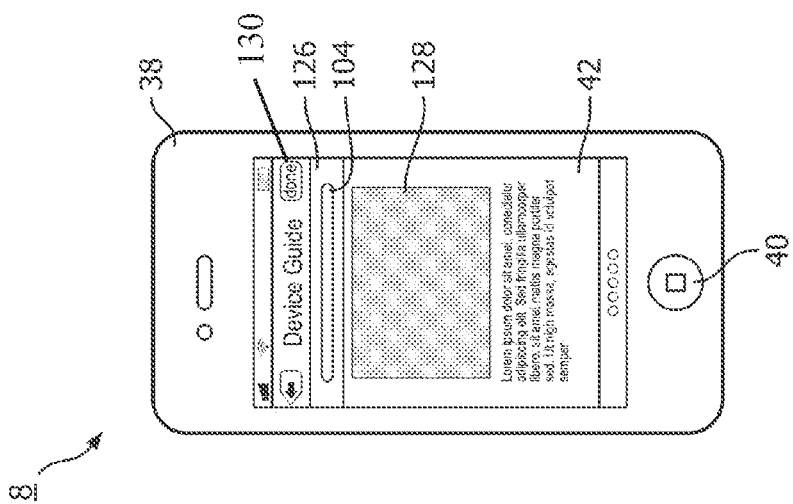

In a third section of the "First Night Guide" portion, called the "Device Guide" section, software application/tool 54 provides information to the user in a device guide screen or screens 126 regarding operation and use of the particular pressure generating device (the components in the dotted lines of FIG. 2) of pressure support system 4. As seen in FIG. 10, device guide screen (or screens) 126 includes a device guide 128 that is selected based on the "Device Number" information that was provided by the user during creation of the user's account. Device guide 128 may include, without limitation, text, photos, drawings, step by step instructions and/or videos. Device guide screen (or screens) 126 also includes a done button 130 that, when selected, enables the user to advance to the next portion of software application/tool 54, which, as described below, is the "home" screen for the software application/tool 54, also referred to as the "sleep" screen.

Figure 11:
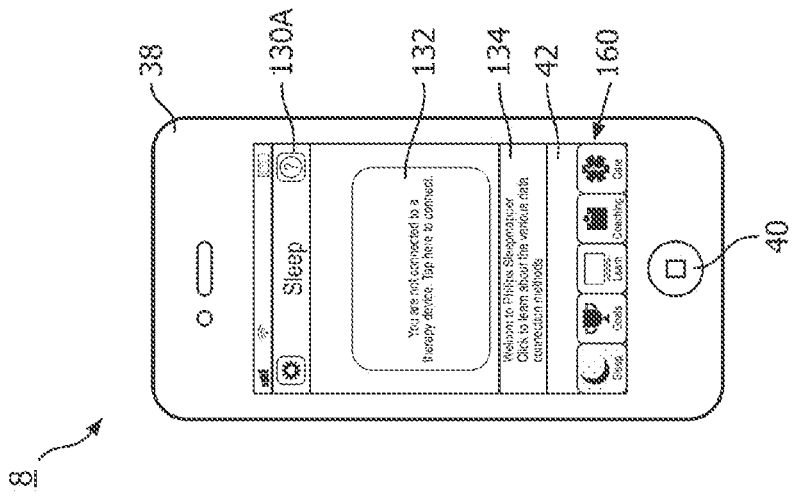
Figure 12:
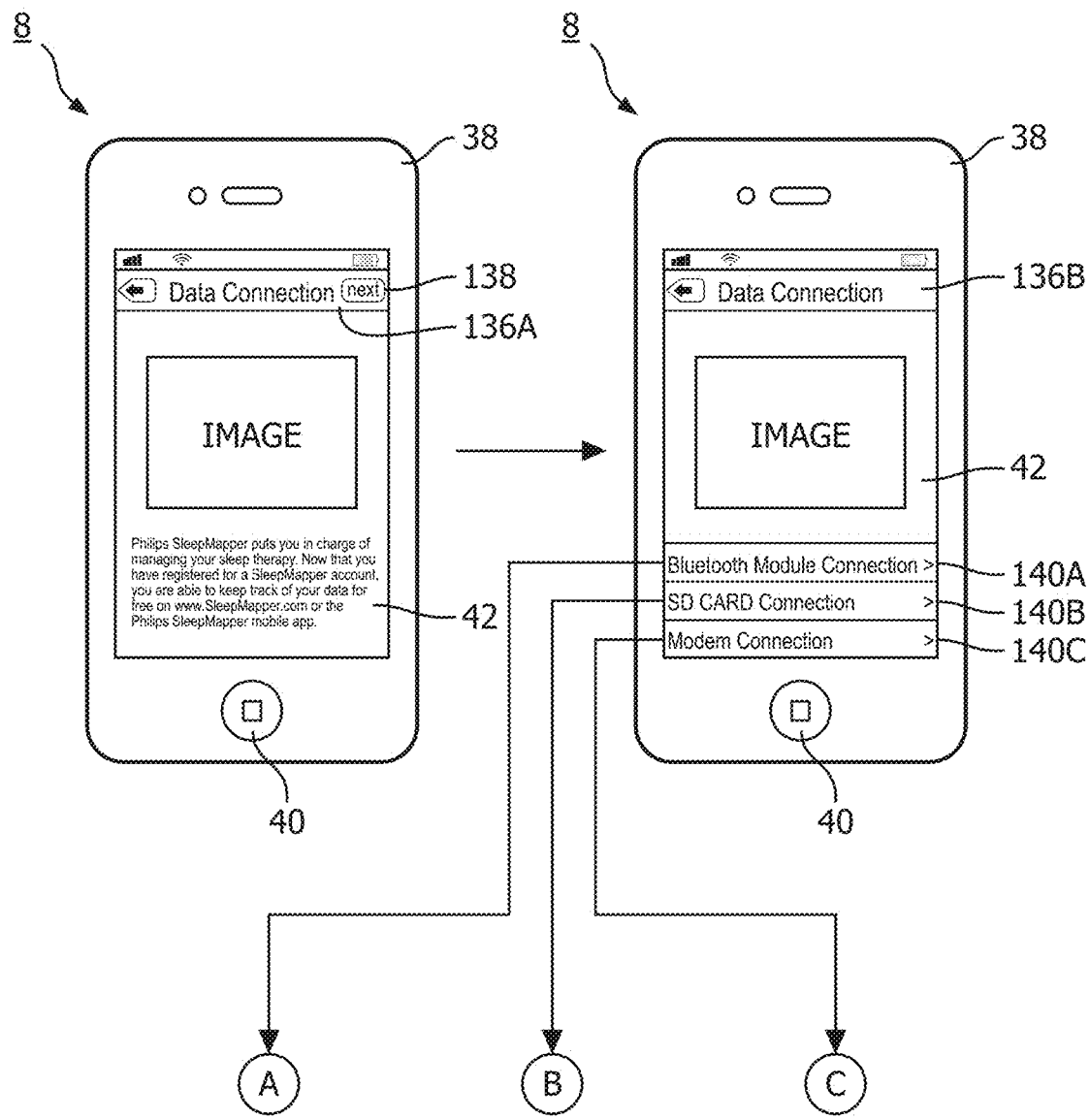
Figure 12:
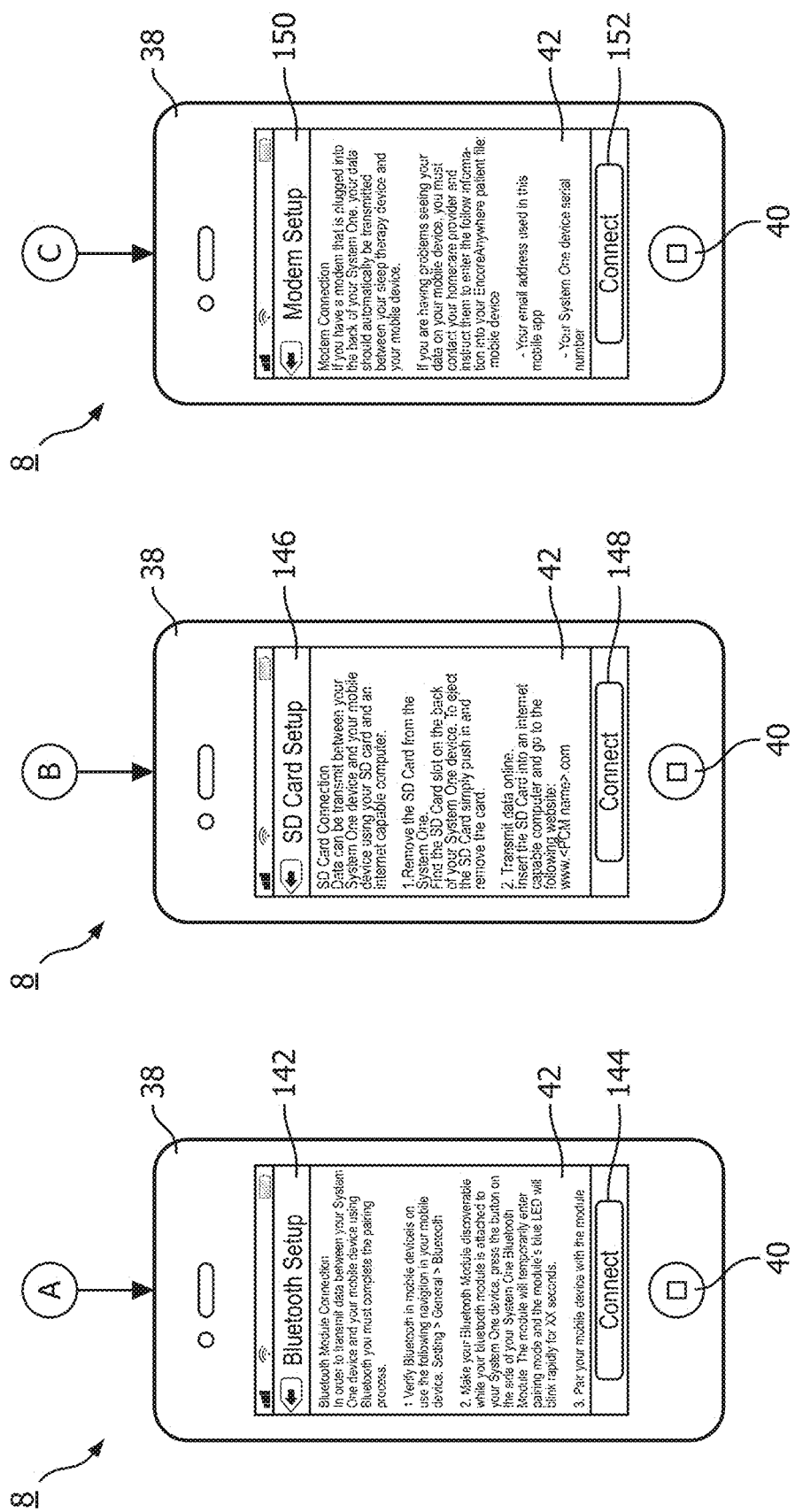

FIG. 11 shows the sleep screen 130A of software application/tool 54 in the illustrated exemplary embodiment. For first time users, sleep screen 130A as shown in FIG. 11 is displayed after completion of the "First Night Guide" portion. It is at this point that the user is able to determine how, in the exemplary embodiment, the raw data from pressure support device 4 is periodically provided to central computer system 6 so that it can be processed into the patient/therapy metrics as described elsewhere herein. In particular, as seen in FIG. 11, the sleep screen 130A at this stage includes a message 132 indicating to the user that a data connection method for their pressure support device 4 must be established, and a message 134, that may be selected by the user, if the user would like to learn more about the different data connection methods. In order to select a data connection method, the user must select ("tap") message 132. When the user does so, data connection screen 136A shown in FIG. 12 is provided on touchscreen display 42. By selecting a next button 138, the user is able to proceed to data connection screen 136B shown in FIG. 12. Data connection screen 136B includes three buttons/messages 140A, 140B, 140C, one for each different data connection method of the non-limiting exemplary embodiment.

More specifically, button/message 140A is for data connection wherein short range wireless communication (Bluetooth® in the illustrated embodiment) between pressure support device 4 and portable electronic device 8 is employed. If button/message 140A is selected, setup screen 142 shown in FIG. 12 is displayed that includes information about that data connection method and a button 144 wherein a user may select that data connection method as the established method for system 2. Button/message 140B is for data connection wherein transfer of data using a portable memory device (SD card in the illustrated embodiment) between pressure support device 4 and PC 10 is employed. If button/message 140B is selected, setup screen 146 shown in FIG. 12 is displayed that includes information about that data connection method and a button 148 wherein a user may select that data connection method as the established method for system 2. Button/message 140C is for data connection wherein transfer of data from pressure support system 4 to central computer system 6 using a modem is employed. If button/message 140C is selected, setup screen 150 shown is FIG. 12 is displayed that includes information about that data connection method and a button 152 wherein a user may select that data connection method as the established method for system 2.

Data connection screen 136B may also include options (i.e., other buttons/messages) for other data connection methods, such as Wi-Fi or another wireless connection option. In addition, software application/tool 54 may be adapted/configured for suggesting the "best" connection method for the user given the particulars of pressure support system 4 or other parts of system 2. For example, a message/button may be provided on data connection screen 136B wherein, when selected by the user, the "best" connection method for the user given the particulars of pressure support system 4 or other parts of system 2 will be suggested to the user on display 42. In one embodiment, the suggested "best" connection method may be based on the known capabilities of the previously identified (as described herein) pressure support system 4 and portable electronic device 8. For example, if the "Device Number" (e.g., serial number) of pressure support system 4 indicates that pressure support system 4 has Bluetooth® or Wi-Fi capability and portable electronic device 8 also has Bluetooth® or Wi-Fi capability, then software application/tool 54 will suggest discovering pressure support system 4 over Bluetooth® or Wi-Fi and selecting that as the established data connection method). If the "Device Number" (e.g., serial number) of pressure support system 4 indicates that pressure support system 4 does not support Bluetooth®/Wi-Fi/etc, then software application/tool 54 will suggest the SD card option as the "best" connection option. As another example, in response to selection of the message/button for suggesting a "best" connection method, portable electronic device 8 would be caused to wirelessly search to see if there is a nearby pressure generating device (e.g., part of pressure support system 4) available on Bluetooth®, Wi-Fi, or some other wireless network, and if so, software application/tool 54 will suggest selecting that as the established data connection method.

Once a data connection method is selected as just described, software application/tool 54 will display sleep screen 130B as shown in FIG. 13. In addition, sleep screen 130B is the screen that will be displayed each time after first use (i.e., after initial set up as described above) that the user launches software application/tool 54 and logs in to his or her account. Thus, after first use (i.e., after initial set up), sleep screen 130B functions as the home screen for software application/tool 54. As seen in FIG. 13, sleep screen 130B includes two main areas, a metrics area 154 and a dynamic messaging area 156.

In metrics area 154, sleep screen 130B displays information relating to certain patient/therapy metrics generated in the exemplary embodiment by central computer system 6. In the illustrated, exemplary embodiment, the following three patient/therapy metrics are employed and information relating thereto is displayed in metrics area 154: (i) a mask fit metric, which is a fit percentage that is determined based on the amount of mask leak that is detected by pressure support system 4, (ii) a therapy metric, which indicates the length of use, in hours, of pressure support device 4 by the user during a period of sleep (e.g., a night) and that is determined based on usage data detected by pressure support system 4, and (iii) an AHI metric, which is an apnea/hypopnea index for a period of sleep (e.g., a night) that is determined based on data measured by pressure support system 4. As is known in the art, the apnea/hypopnea index is calculated by dividing the number of events (apnea or hypopnea) by the number of hours of sleep. It will be understood that the three metrics described above are meant to be exemplary only, and that other, different patient/therapy metrics in place of and/or in addition to those described above may be employed within the scope of the present invention. In sleep screen 130B, the metric value for the most recent period of sleep (e.g., the prior night) is displayed in metrics area 154.

In addition, a user may access the history for any of the individual metrics by selecting (e.g., pressing and holding) the button area 155 beneath the metric that includes the graphical icon. This is demonstrated for the therapy metric in FIG. 14, which shows sleep screen 130C. As seen in FIG. 14, in the illustrated embodiment, if eight periods (e.g., eight days) or more of data is available, the therapy metric for fourteen periods (e.g., fourteen days) of usage is shown in graphical form. If less than eight periods (e.g., eight days) of data is available, the therapy metric for the period of usage over which data is available (e.g., seven periods (e.g., seven days) of usage) is shown in graphical form. A target line 158 for the metric (which represents a predetermined target value for the metric) is provided for quick reference by the user. In the exemplary embodiment, the target for the therapy metric is driven as follows: first seven periods/days, target=2 hrs; every seven days after, target=1.2×(previous seven periods/days total usage)/7; target no longer shown when target=7 hrs. Similar history data and targets may be displayed for the mask fit and AHI metrics.

As seen in FIGS. 13 and 14, dynamic messaging area 156 includes a scalable list of dynamic messages 158. In the illustrated embodiment, each dynamic message 158 contains two lines of text and may include a link triggering another portion of software application/tool 54 and/or providing access to additional content, such as third party video content.

For example, a dynamic message 158 may indicate problem or issue with use of pressure support system 4 based on one or more of the patient/therapy metrics and may provide information and/or a link to a solution for the problem. For instance, if the mask fit metric is determined to be below a certain threshold level (e.g., <75%), a dynamic message 158 may inform the user of the problem ("It seems you have a poor mask fit") and provide a link that triggers a troubleshooting section/guide of software application/tool 54 (described elsewhere herein) that would provide instructions, links to videos or relevant online discussion forums (e.g., selected message boards), and/or other information on how to address the leak issue. Alternatively, if the therapy metric is determined to be below a certain threshold level (e.g., <2 hr), that may indicate that the user is having issues with mask fit and/or comfort (e.g., pressure points, red marks, mask instability, tubing issues) and/or therapy comfort (difficulty exhaling, difficulty falling asleep, side effects such as dry or wet nose, nasal congestion, gassy bloated feeling, frequent wakes ups). In response, a dynamic message 158 may be provided informing the user of the problem ("It seems your usage is low. This may be due to . . . ") and providing a link that triggers the troubleshooting section/guide of software application/tool 54 that would provide instructions, links to videos or relevant online discussion forums (e.g., selected message boards), and/or other information on how to address the usage issue. According to an aspect of the exemplary embodiment, the troubleshooting would be customized based on the particular equipment of pressure support system 4 that has been set/specified as described elsewhere herein (e.g., the troubleshooting section/guide would be specific to the mask type and model number that has been previously set). For example, the user may be presented with links to online discussion forums (e.g., message boards) that are particular to the user's equipment.

In another example, a dynamic message 158 may indicate that a new target for a patient/therapy metric has been set (the new target may be listed or a link to the new target may be provided) or that a customized goal (described elsewhere herein) for a patient/therapy metric has been achieved.

In still another example, a dynamic message 158 may provide a notification that a component (e.g., the mask or patient interface 20 or delivery conduit 18, or an accessory such as a humidifier or filter) of pressure support system 4 needs to be cleaned, serviced and/or replaced. Such notifications may be based simply on the passage of time (e.g., a month) or may be based on total actual usage parameters (e.g., a certain number of hours of actual use), and may be custom set by the user or a DME supplier, or may be default settings in software application/tool 54. In addition, such notifications may provide a link to ordering options (for example, selecting the notification press pushes the user to a DME-specific ordering website or pushes an automatic order (electronic) to a predetermined DME supplier).

In yet another example, a dynamic message 158 may contain a recommendation to watch one or more videos or to access and use the device guide and/or mask guide portions of software application/tool 54 (again, customized for the particular equipment of pressure support system 4 that has been set/specified as described elsewhere herein). The content of such a dynamic message 158 may be updated over time by either the provider of software application/tool 54 or by a DME supplier so that the content (the specific video content or the specific device guide and/or mask guide content) is not stale and can be customized per the relevant DME supplier. Also, a dynamic message 158 may be used for advertising for components for use in pressure generating system 4 (e.g., newest mask designs . . . "let us show you the latest full face mask available . . . ").

In yet another example, a dynamic message 158 may contain suggestions made on the patient/therapy metrics generated in the exemplary embodiment by central computer system 6 (e.g., the monitored AHI) or on any other monitored parameter from pressure support system 4 that corresponds to the possible physiological condition of the patient. For example, if the patient is showing a much higher percent of the night in Cheyne-Stokes respiration (CSR) recently or has a higher AHI or any other monitored parameter, software application/tool 54 may be configured to generate a dynamic message 158 that encourages the patient to either contact their physician or DME supplier and/or that pushes the patient towards a questionnaire (e.g. Are you short of breath?, Do you have trouble breathing while walking?) that then leads to contacting their physician if the monitored parameter(s) and the questionnaire suggest a high probability of a worsening medical condition (e.g. asthma, pulmonary edema, etc.).

In addition, as seen in FIGS. 11, 13 and 14, among others, a navigation section 160 is provided at the bottom of touchscreen display 42. Navigation section 160 includes a number of tabs (labeled "Sleep", "Goals", "Learn", "Coaching" and "Care" in the illustrated embodiment), wherein each tab corresponds to a major portion of software application/tool 54. Selection of those tabs allows the user to selectively navigate to those portions of software application/tool 54. Thus, selection of the "Sleep" tab will take the user to the sleep screen 130B (FIG. 13).

According to a further aspect, software application/tool 54 also includes a "Goals" portion wherein a user is able to set goals based on the patient/therapy metrics and track progress toward those goals. The user may access the "Goals" portion by selecting the "Goals" tab of navigation section 160. A goals screen 162A, as shown in FIG. 15, is displayed on touchscreen display 42 when the "Goals" tab is selected. Goals screen 162A includes a navigation section 164 having tabs that enable navigation among the various sections of the "Goals" portion described below.

In the "My Goals" section, a number of goal sections 166 are displayed. Each goal section 166 corresponds to a specific goal that is based on the patient/therapy metrics, and each goal section includes a progress bar 168 which track progress toward those goals. In the exemplary embodiment, four different predetermined goal categories are utilized (shown in FIG. 15) and the user is able to custom set the goal value for each category. Those goal categories are: (i) #days with 4+ hrs of use of pressure support system 4 in month, (ii) consecutive days of use of pressure support system 4, (iii) consecutive days with 4+ hrs of use of pressure support system 4, and (iv) consecutive days of use of pressure support system 4 with >75% mask fit. It will be appreciated that other goal categories are also possible. In the exemplary embodiment, each progress bar 168 in each goal section 166 is updated periodically (e.g., each day) based on the metrics data that is received from central computing system 6. In the exemplary embodiment, the user is able to set and change goal values for each goal section 166 using a set goal screen 170 as shown in FIG. 16. Each set goal screen 170 may be accessed by selecting the corresponding goal section 166, and the "−" and "+" buttons 171 and 173, respectively, may be used to adjust the goal values. Alternatively, software application/tool 54 may be configured to automatically set goals based on data measured by pressure support system 4 and/or prior patient/therapy metric value.

Figure 21:
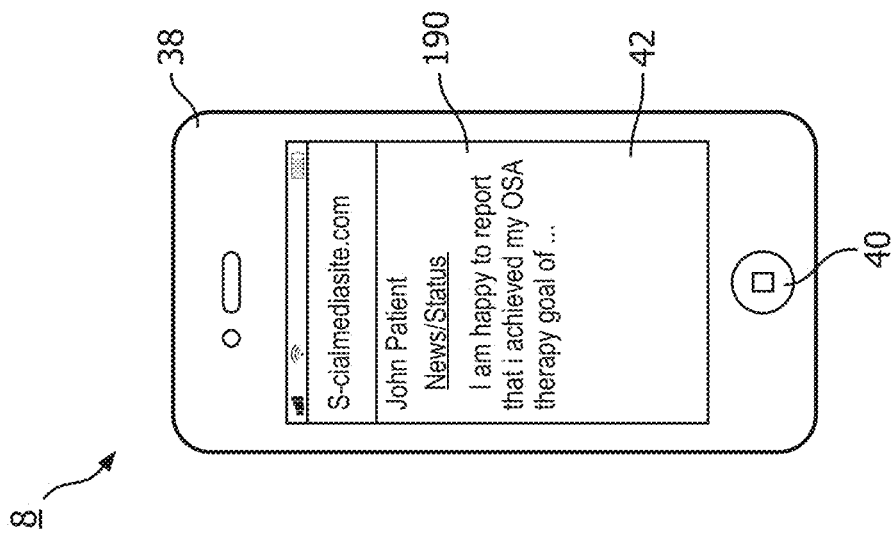
Figure 20:
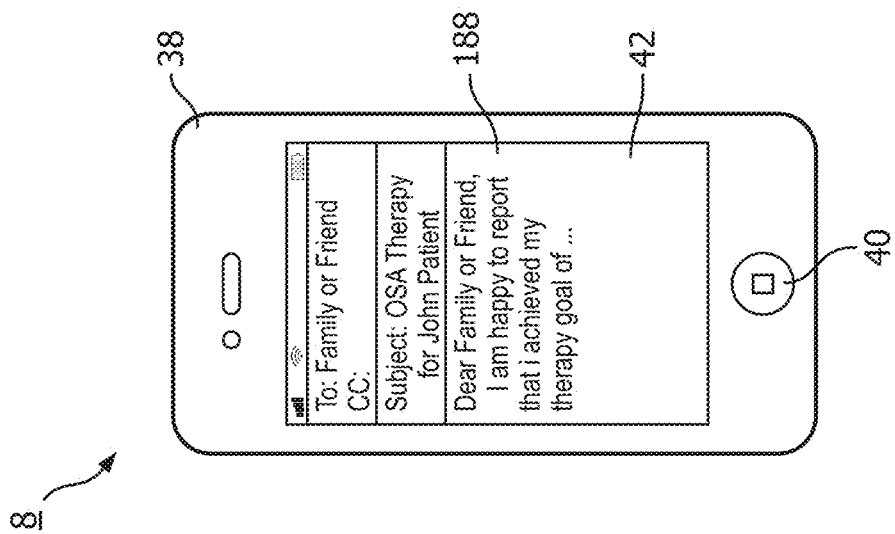

Referring to FIG. 17, when a goal in a goal section 166 is achieved, a message 172 is provided on goals screen 162A that includes a done button 174 and an achievement icon (e.g., a cup) 176. In the exemplary embodiment, if the user selects (presses) done button 174 provided on goals screen 162A, achievement icon 176 animates into the achievement tab of navigation section 164 as shown in FIG. 18. When the user selects the achievement tab of navigation section 164, a list 178 of all of the achieved goals is provided on goal screen 162B shown in FIG. 19. As seen in FIG. 19, each achieved goal is provided in an associated achieved goal section 180 which, in the exemplary embodiment, describes the achieved goal. As shown in FIG. 19, selecting any particular achieved goal section 180 activates a menu 182 that includes two action icons, namely a mail icon 184 and a trash icon 186. As shown in FIG. 20, selecting mail icon 184 activates an email application of portable electronic device 8 and causes an email message 188 addressed to a preselected recipient or recipients to be pre-populated with a message indicating that the user has achieved the particular goal. Thus, the user is able to designate one or more individuals (e.g., a family member such as a parent or child or a friend) who are to receive news of such achievements so that they can be kept abreast of the actual use of pressure support system 4 and the therapy being received by the user. In an alternative embodiment, additional icons can be provided for automatically generating and posting messages (e.g., a message 190 shown in FIG. 21) indicating that the user has achieved the particular goal on social media outlets/sites, such as, without limitation, Twitter® and Facebook®, or for automatically generating and sending a message (to one or more predetermined individuals) using an alternative electronic messaging service such as the short message service message (SMS) or the multimedia messaging service (MMS). Selecting trash icon 186 causes the associated achieved goal section 180 to be deleted.

In addition to the achievement of goals as just described, other therapy information, such as, without limiting, the patient/therapy metrics described herein, may be automatically and periodically emailed to one or more individuals (i.e., a third party outside of the patient, home care provider and physician) and/or posted to a social media outlet/site by portable electronic device 8.

According to still a further aspect, software application/tool 54 also includes a "Learn" portion wherein a user is able to obtain information about his or her sleep disordered breathing condition and/or pressure support system 4 that they are using to treat that condition. The user may access the "Learn" portion by selecting the "Learn" tab of navigation section 160. A learn screen 192A, as shown in FIG. 22, is displayed on touchscreen display 42 when the "Learn" tab is selected. Learn screen 192A includes a navigation section 194 having tabs ("Apnea", "Equipment" and "Troubleshoot") that enable navigation among the various sections of the "Learn" portion described below.

When the "Apnea" tab is selected, a list 196 as shown in FIG. 22 comprising a number of links to educational videos and/or documents relating to the user's sleep disordered breathing condition (e.g., OSA) is provided. Similarly, when the "Equipment" tab is selected, a list 198 as shown in FIG. 23 (on learn screen 192B) comprising a number of links to educational videos and/or documents relating to the particular components of pressure support system 4 being used by the user (as set by the user as described elsewhere herein) is provided. In addition, as seen in FIG. 23, list 198 also includes links to the "Device Guide" and "Mask Guide" sections of software application/tool 54 described elsewhere herein. Again, the "Device Guide" and "Mask Guide" sections will be particular to the components of pressure support system 4 being used by the user as set by the user as described elsewhere herein. When the "Troubleshoot" tab is selected, the user will be guided by software application/tool 54 through a hierarchy of options for addressing various issues that the user may be experiencing during therapy using pressure support system 4 that ends up on either a video link or a document. In the exemplary embodiment, the issues that may be addressed (and for which suggested solutions are provided) include mask leak, mask discomfort, mask removal during sleep, mask instability, pressure points/marks on the user's face, difficulty exhaling, difficulty falling asleep, insufficient therapy pressure, tubing issues such as limited movement and heavy feel, and side effects such as dry or wet nose, nasal congestion, gassy bloated feeling, and/or frequent wakes ups. According to an aspect of the exemplary embodiment, the troubleshooting would be customized based on the particular equipment of pressure support system 4 that has been set/specified as described elsewhere herein (e.g., the troubleshooting would be specific to the mask type and model number that has been previously set or the model of the pressure generating device of pressure support system 4).

In yet another aspect of the exemplary embodiment, software application/tool 54 also includes a "Coaching" portion wherein Motivational Enhancement Therapy (MET) is employed to encourage better therapy compliance by the user. The user may access the "Coaching" portion by selecting the "Coaching" tab of navigation section 160. The "Coaching" portion employs proprietary techniques aimed at increasing compliance by asking patient specific questions about their motivation to use pressure support therapy and delivering the patient's own answers back to them once they begin their treatment. The "Coaching" portion will guide the patient through a specific protocol at predetermined "virtual interventions." In the exemplary embodiment, the virtual interventions occur when it has been determined, based on the therapy metric, that the patient has used pressure support system 4 less than a certain amount of time (e.g., 2 hrs.) during the previous relevant period. Also in the exemplary embodiment, the following three MET techniques will be incorporated: (i) motivation, wherein at a virtual intervention point (e.g., the first time the patient's usage is low) the patient's motivation to use sleep therapy is rated on a 1-10 scale, and then the patient is questioned about the rating and, in particular, their main motivation for using therapy, (ii) heart risk, wherein at another virtual intervention point (e.g., the second time the patient's usage is low) the patient is educated using a study comparing mortality rates of patients, and then the patient is questioned about how the data from the study impacted them, and (iii) feelings, wherein at another virtual intervention point (e.g., the third time the patient's usage is low) the patient is shown a video clip of an actual patient experiencing an apnea event, and then the patient is questioned about how the video made them feel. Thereafter, according to an aspect of software application/tool 54, when it is determined, based on the therapy metric, that the patient has used pressure support system 4 less than a certain amount of time (e.g., 2 hrs.) during the previous relevant period, the patient may be provided with reminder/notifications of one or more of (i) their main motivation for using therapy (as entered by them), (ii) their statements about how the data from the study impacted them (as entered by them), and (iii) their statements about how the video of the patient suffering an actual apnea made them feel.

In still another aspect of the exemplary embodiment, software application/tool 54 also includes a "Care" portion wherein the patient's home care provider may choose to provide a mechanism (e.g., branded with their logo) by which the patient is able to contact them directly. The user may access the "Care" portion by selecting the "Care" tab of navigation section 160. In the illustrated embodiment, when the user selects the "Care" tab of navigation section 160, a care screen 200 as shown in FIG. 24 is provided on touchscreen display 42. Care screen 200 includes a call button 202 and an email button 204. Selecting call button 202 activates a phone application of portable electronic device 8 and causes a phone call to be made to the user's home care provider. Selecting email button 204 activates an email application of portable electronic device 8 and causes an email to the home care provider's email address to be generated, with a portion that may be filled in by the user to include a question, etc.

Thus, as described in detail herein, system 2 provides any easy to use, software based mechanism for a patient suffering from a condition that requires use of a respiratory therapy device (e.g., a sleep disordered breathing condition, such as OSA, CSA, CSR, COPD, or a condition that requires home ventilation therapy) to effectively manage their condition and treatment by providing customized/personalized education and feedback regarding their condition and their specific therapy wherein use of the mechanism is likely to increase therapy compliance and therefore improve treatment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of providing information to a patient, wherein the patient uses a pressure support system structured to provide therapy to the patient to treat a condition of the patient by delivering a flow of breathing gas to the patient, comprising acts of:
    establishing in a computing device a goal based on a patient/therapy metric relating to treatment using the pressure support system;
    obtaining in the computing device patient/therapy metric data, wherein the patient/therapy metric data is formed by processing data measured by the pressure support system during the provision of therapy to the patient; and
    displaying goal information on a display of the computing device, the goal information indicating progress toward the goal and being based on the patient/therapy metric data,
    wherein the patient/therapy metric data includes at least one of a first metric relating to a degree of mask leak, and a second metric indicating a number of apnea and/or hypopnea events experienced by the patient during a certain period of time.

2. The method according to claim 1, wherein the first metric includes a mask fit metric based on a measurement of mask leak.

3. The method according to claim 1, wherein the second metric includes an apnea/hypopnea index.

4. The method according to claim 1, wherein the goal includes one of: (i) a number of days with at least a certain amount of use of the pressure support system in a certain time period, (ii) a number of consecutive days of use of the pressure support system, (iii) a number of consecutive days with at least the certain amount of use of the pressure support system, and (iv) a number of consecutive days of use of the pressure support system when the first metric is at least a certain value.

5. The method according to claim 1, further comprising an act of, responsive to determining that the goal has been achieved, automatically generating in the computing device an electronic message indicating that the goal has been achieved.

6. The method according to claim 5, wherein the electronic message is at least one of: (i) an electronic mail message, an SMS message or an MMS message directed to a predetermined recipient, and (ii) a message posted on a predetermined publicly accessible third party online system.

7. The method according to claim 1, wherein the computing device is one of a portable electronic device or a personal computer.

8. The method according to claim 1, wherein the act of obtaining in the computing the device patient/therapy metric data comprises an act of receiving the device patient/therapy metric data from a computer system remote from the computing device and the pressure support system.

9. The method according to claim 8, wherein the computer system forms the device patient/therapy metric data.

10. The method according to claim 8, wherein: (i) the computer system receives the data measured by the pressure support system from the computing device and the computing device receives the data measured by the pressure support system directly from the pressure support system, (ii) the computer system receives the data measured by the pressure support system directly from the pressure support system, or (iii) the computer system receives the data measured by the pressure support system from a personal computer and the personal computer receives the data measured by the pressure support system directly from the pressure support system.

11. The method according to claim 10, wherein in the case of (i), the computing device receives the data measured by the pressure support system directly from the pressure support system by way of a short range wireless transmission, and in the case of (iii), the personal computer receives the data measured by the pressure support system directly from the pressure support system by way of transfer using a portable memory device or by way of a short range wireless transmission.

12. The method according to claim 1, wherein the establishing act includes at least one of acts of (i) receiving input into the computing device that establishes the goal, and (ii) automatically setting the goal in the computing device based on certain data measured by the pressure support device and/or past patient/therapy metric data.

13. A computing device configured to provide information to a patient, wherein the patient uses a pressure support system structured to provide therapy to the patient to treat a condition of the patient by delivering a flow of breathing gas to the patient, the computing device comprising:

a display; and
a processor apparatus including a processor and a memory, the memory storing one or more routines executable by the processor, the one or more routines being adapted to:
 establish a goal based on a patient/therapy metric relating to treatment using the pressure support system;
 obtain patient/therapy metric data, wherein the patient/therapy metric data is formed by processing data measured by the pressure support system during the provision of therapy to the patient;
 generate goal information, the goal information indicating progress toward the goal and being based on the patient/therapy metric data; and
 cause the display to display the goal information,
wherein the patient/therapy metric data includes at least one of a first metric relating to a degree of mask leak, and a second metric indicating a number of apnea and/or hypopnea events experienced by the patient during a certain period of time.

14. The computing device according to claim 13, wherein the computing device is one of a portable electronic device or a personal computer.

15. The computing device according to claim 13, wherein the first metric includes a mask fit metric based on a measurement of mask leak.

16. The computing device according to claim 13, wherein the second metric includes an apnea/hypopnea index.

17. The computing device according to claim 13, wherein the goal includes one of: (i) a number of days with at least a certain amount of use of the pressure support system in a certain time period, (ii) a number of consecutive days of use of the pressure support system, (iii) a number of consecutive days with at least the certain amount of use of the pressure support system, and (iv) a number of consecutive days of use of the pressure support system when the first metric is at least a certain value.

18. The computing device according to claim 13, wherein the one or more routines are further adapted to, responsive to determining that the goal has been achieved, automatically cause the computing device to generate an electronic message indicating that the goal has been achieved.

19. The computing device according to claim 17, wherein the electronic message is at least one of: (i) an electronic mail message, an SMS message or an MMS message directed to a predetermined recipient, and (ii) a message posted on a predetermined publicly accessible third party online system.

20. The computing device according to claim 13, wherein the one or more routines are adapted to obtain the device patient/therapy metric data by receiving the device patient/therapy metric data from a computer system remote from the computing device and the pressure support system.

* * * * *